(12) United States Patent
Liberman et al.

(10) Patent No.: US 8,480,894 B2
(45) Date of Patent: Jul. 9, 2013

(54) DESALINATION SYSTEM AND ELEMENTS THEREOF

(75) Inventors: Boris Liberman, Tel Aviv (IL); Miriam Faigon, Kfar Saba (IL); Yosef Pinhas, Hadera (IL); Maya Ilevicky-Ozel, Tel Aviv (IL); Yacov Ben-Yaish, Zoran (IL); Erez Reuveni, Ein Hahoresh (IL)

(73) Assignee: I.D.E. Technologies Ltd., Kadima (IL)

( * ) Notice: Subject to any disclaimer, the term of this patent is extended or adjusted under 35 U.S.C. 154(b) by 313 days.

(21) Appl. No.: 12/812,193

(22) PCT Filed: Jan. 11, 2009

(86) PCT No.: PCT/IL2009/000046
§ 371 (c)(1),
(2), (4) Date: Jul. 8, 2010

(87) PCT Pub. No.: WO2009/087642
PCT Pub. Date: Jul. 16, 2009

(65) Prior Publication Data
US 2010/0282676 A1    Nov. 11, 2010

Related U.S. Application Data

(60) Provisional application No. 61/006,386, filed on Jan. 10, 2008.

(51) Int. Cl.
*B01D 69/10* (2006.01)
*B01D 65/10* (2006.01)
*C02F 1/44* (2006.01)
*B01D 63/12* (2006.01)
*C02F 103/08* (2006.01)

(52) U.S. Cl.
CPC .............. *B01D 63/12* (2013.01); *B01D 65/102* (2013.01); *C02F 1/441* (2013.01); *C02F 2103/08* (2013.01); *C02F 2209/008* (2013.01)
USPC .............................. 210/253; 210/87; 210/232

(58) Field of Classification Search
CPC ........ B01D 63/12; B01D 65/102; C02F 1/441; C02F 2103/08; C02F 2209/008
USPC ...................... 210/321.64, 134, 652, 253, 87
See application file for complete search history.

(56) References Cited

U.S. PATENT DOCUMENTS

| 4,033,878 | A | * | 7/1977 | Foreman et al. | .......... 210/321.74 |
| 4,559,138 | A | * | 12/1985 | Harms, II | ...................... 210/316 |
| 6,942,797 | B1 | | 9/2005 | Chancellor | |

FOREIGN PATENT DOCUMENTS

| WO | WO 98/23361 A1 | 6/1998 |
| WO | WO9823361 A1 * | 6/1998 |
| WO | WO 03/039708 A1 | 5/2003 |
| WO | WO2005082497 A1 * | 9/2005 |
| WO | WO2007030647 A2 * | 3/2007 |

OTHER PUBLICATIONS

Yun et al., Desalination 189 (2006) 141-154.*
International Search Report Dated May 27, 2009 corresponding to International Application PCT/IL2009/000046.

* cited by examiner

*Primary Examiner* — Bobby Ramdhanie
*Assistant Examiner* — Denise R Anderson
(74) *Attorney, Agent, or Firm* — Graeser Associates International Inc; Dvorah Graeser

(57) ABSTRACT

According to one aspect of the present invention, there is provided a desalination system comprising a plurality of elongated pressure vessels (PV). Each PV has a longitudinal axis, oriented such that the longitudinal axis thereof is of a vertical orientation. Each of the PVs is adapted to receive therein a plurality n of desalination membranes. The membranes located above the lowermost membrane within the PV have a total weight allowing them to function as a mechanism limiting axial expansion of the lowermost membrane, whereby the PV is free of any additional limiting mechanism.

13 Claims, 24 Drawing Sheets

"Existing Art"

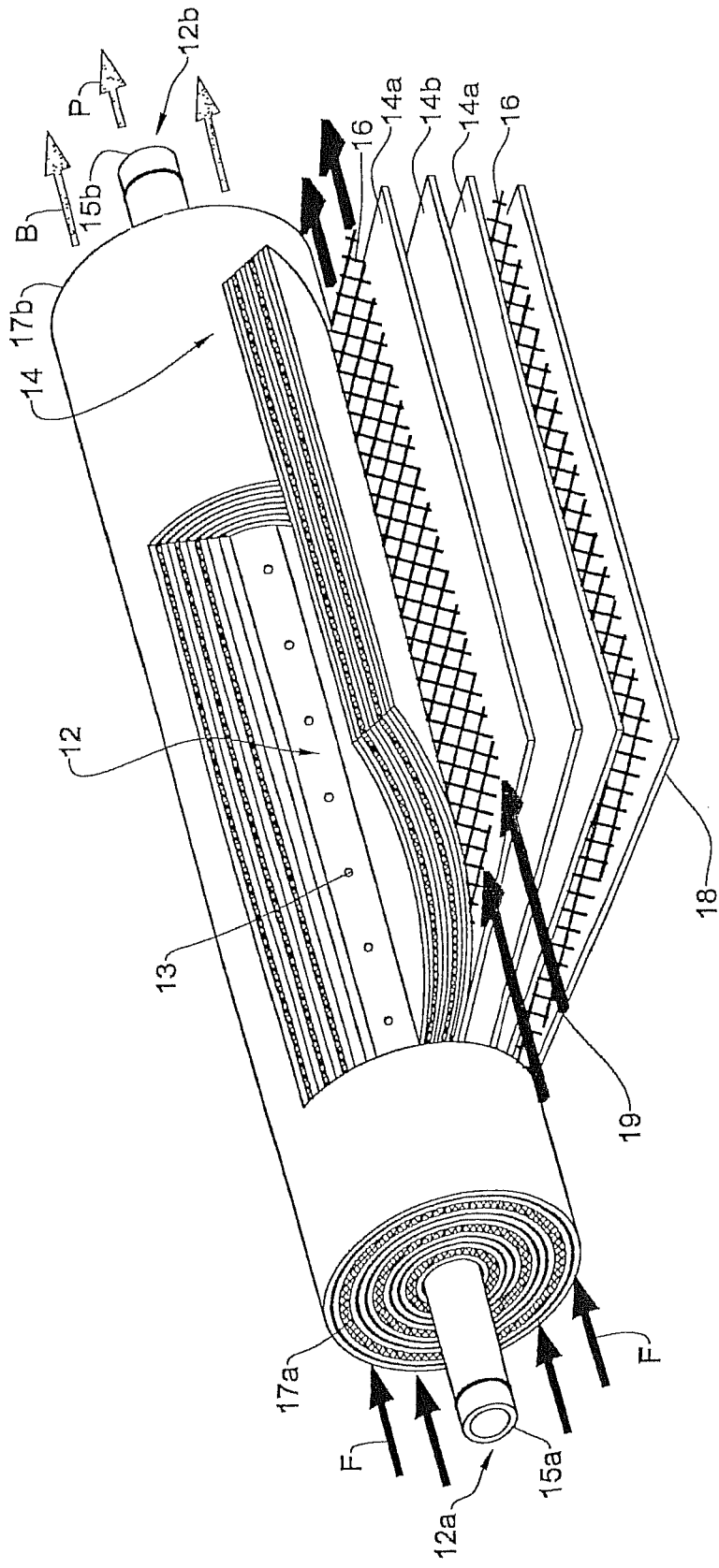
FIG. 2 "Existing Art"

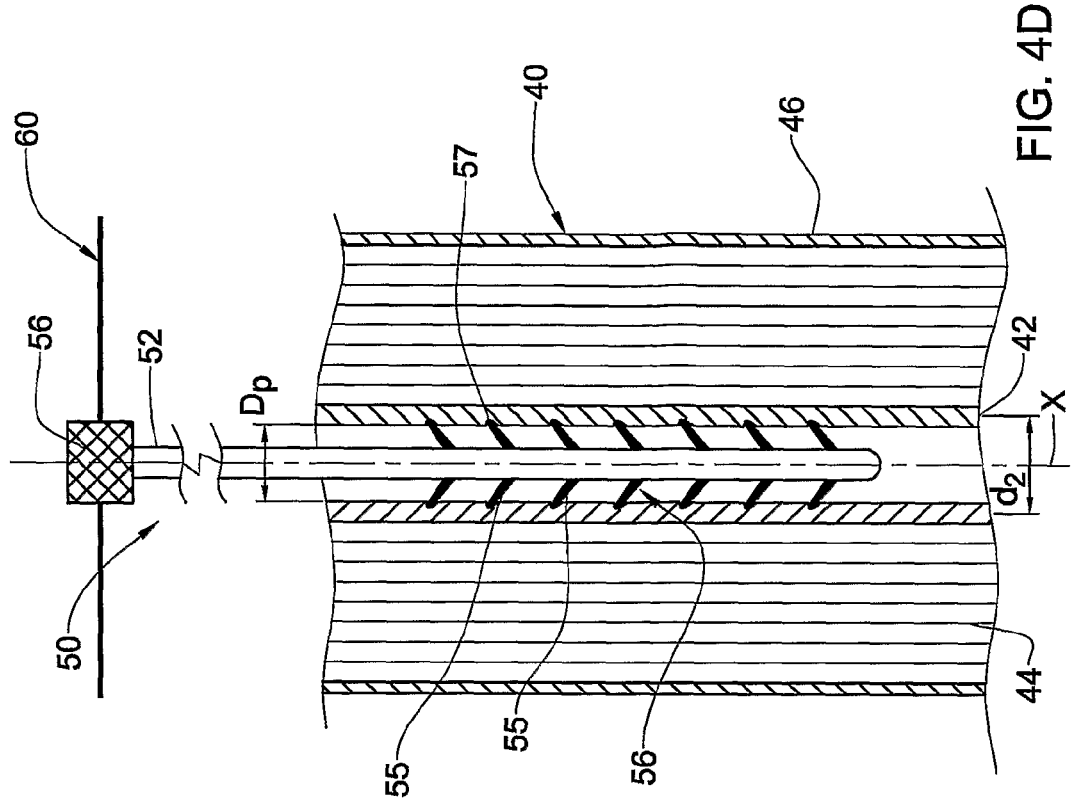
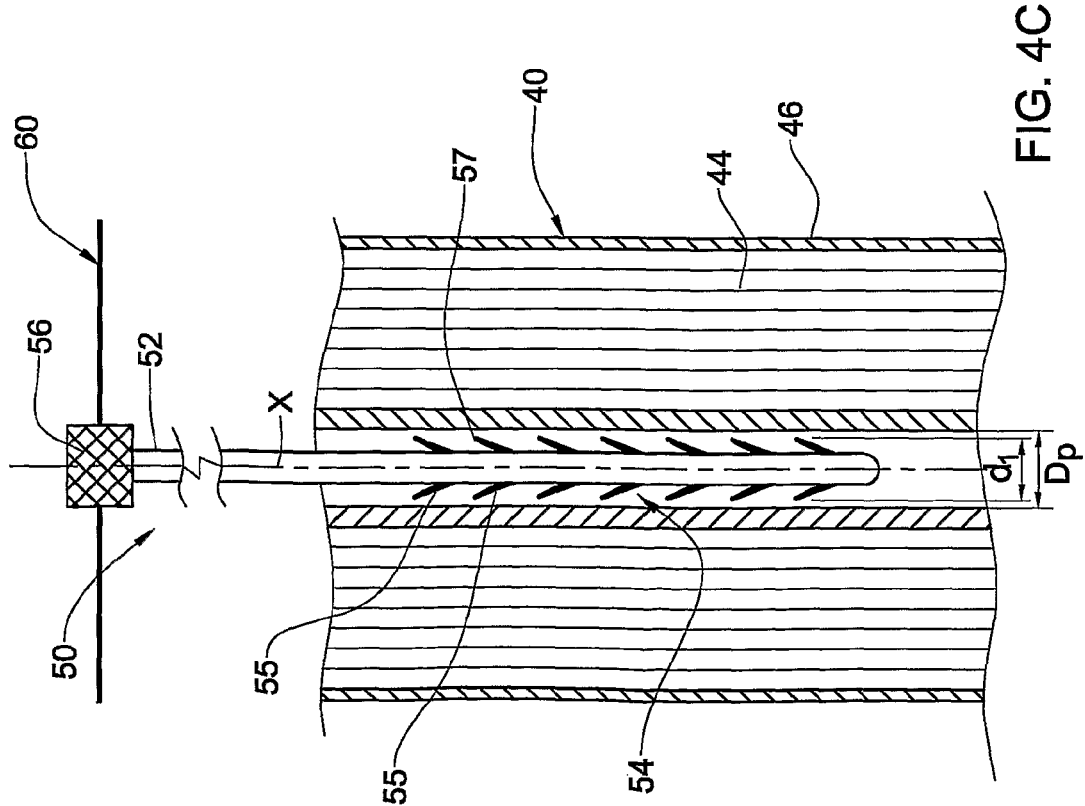
FIG. 4C
FIG. 4D

DESALINATION SYSTEM AND ELEMENTS THEREOF

CROSS REFERENCE TO RELATED APPLICATIONS

This U.S. patent application claims priority to PCT application serial number WO/2009/087642, filed on Jan. 11, 2008, which in turn claimed priority to U.S. provisional application Ser. No. 61/006,386, filed on Jan. 10, 2008, both of which are incorporated by reference herein.

FIELD OF THE INVENTION

This invention relates to desalination systems, in particular reverse osmosis (RO) desalination systems, including a plurality of pressure vessels, desalination membranes used therein, equipment for mounting said membranes and means for estimating their operational conditions.

BACKGROUND OF THE INVENTION

RO desalination systems are well known in the art. With reference to FIG. 1, an example of an RO desalination system is shown:

The RO desalination system of the kind described above generally designated at 1 comprises a plurality of pressure vessels (PVs) 2 held by a support construction 3, the construction 3 comprising holders 4 for supporting each of the PVs 2 in a horizontal orientation. Each of the PVs is in fact suspended by the support construction 3 so that it is supported from underneath at several points along its length.

Each PV 2 has front and rear ends and has a centrally disposed permeate tube connected to a front product line 5 at the front end of the PV and to a rear product line (not seen) at the rear end of the PV. Each PV 2 is further connected at its front end to a feed line 6 for supplying to the PC raw fluid to be desalinated, and at its rear end to a brine (brine) line (not seen).

Each of the PVs 2 has a plurality of RO membranes 10 mounted therein, whose typical design is shown in FIG. 2. As seen in FIG. 2, the membrane 10 comprises a perforated permeate tube 12 with a multi-layer membrane sheet 14 wound thereon constituting a membrane core, and an encapsulating outer shell 18.

The wound multi-layer membrane sheet 14 defines a reject side on one surface thereof, coming in contact with the feed water, and a permeate side, on the opposite surface thereof, coming in contact with feed water which has passed through the sheet by reverse osmosis, i.e. permeate. The permeate tube 12 is formed with holes 13 adapted for collecting said permeate, which is adapted for withdrawal from the PV via its front and rear central ports 12a and 12b constituted respectively, by front and rear ends of the permeate tube 12 of the membrane 10.

The multi-layer membrane sheet 14 comprises two membrane layers 14a, a permeate layer 14b positioned therebetween, and a feed spacer 16. The multi-layer membrane sheet 14 is wound on the permeate tube 12, its front end 12a being adapted for fluid communication with the feed line 6, constituting thereby a circumferential, feed inlet port 17a of the PV for conducting raw fluid to be desalinated thereto, and its rear end 12b being adapted for fluid communication with the brine line, constituting thereby a circumferential, brine outlet port 17b of the PV for the withdrawal of the brine therefrom.

In operation, feed water F is provided to the circumferential, feed inlet port 17a at the front end 12a of the PV, to flow axially in the direction of arrows 19. Permeate P is collected by the permeate tube 12 to exit through the front and rear central ports 15a, 15b, respectively, and brine (sometimes referred to as 'concentrate') B is removed through the circumferential outlet port 17b at the rear end 12b of the PV.

In assembly, the membrane 10 is located within the PV 2 such that the front and rear permeate ports 15a, 15b are connected to the front and rear permeate lines 5 respectively, the front circumferential port 17a is connected to the feed line 6, and the rear circumferential port 17b is connected to the brine line.

When loading a membrane 10 into the PV 2, the membrane 10 is inserted into the PV 2 horizontally, and is displaced within the PV 2 until it reaches its desired location therein. When unloading a membrane 10, both ends of the PV 2 are opened, whereby the membrane 10 may be pushed from one side of the PV 2 to exit from the other side thereof.

However, there have been known designs in which PVs are disposed vertically, i.e. the PV having a top end and a bottom end, and wherein loading and unloading of membranes was performed through the top end of the PV. Since loading and unloading of membranes is a generally complicated and time consuming process, such PVs are known to employ a small number of membranes, e.g. one or two, and of smaller diameter (and thus of correspondingly smaller weight).

SUMMARY OF THE INVENTION

According to different aspects of the present invention described below there are provided desalination systems, desalination membranes, arrangements for mounting desalination membranes in a desalination system, methods of their operations and methods for monitoring operation thereof which are particularly suitable for reverse osmosis (RO) desalination, but may be used in other types of desalination systems such as nano filtration (NF), micro filtration (MF) and ultra filtration (UF). It is suitable for spiral membrane described in detail in this description and suitable to hollow fiber membranes as well.

According to one aspect of the present invention, there is provided a desalination system comprising a plurality of elongated pressure vessels (PV) each having a longitudinal axis, oriented such that the longitudinal axis thereof is of a vertical orientation, each of said PVs being adapted to receive therein a plurality n of desalination membranes, the membranes located above the lowermost membrane within the PV having a total weight allowing them to function as a mechanism limiting axial expansion of the lowermost membrane, whereby the PV is free of any additional limiting mechanism.

It should also be noted that due to the vertical orientation of the PVs, and the parameters n and D, the weight of the membranes also allows preventing displacement of the membranes within the PV during start and finish of the desalination process.

Preventing thermal expansion of the membranes, as well as displacement thereof within the PV prevents twist of the o-rings which insulate the high pressure seawater area from low pressure desalinated product area, a twist which may cause loss of insulation and intrusion of seawater in to desalinated product.

In addition, the above arrangement allows eliminating the need for a shimming assembly adapted to prevent displacement of the membranes within the PV. Existing manual shimming methods are based on spacers and washers which are not effective as it requires opening the PVs several times a year for re-shimming. Existing automatic shimming mechanisms are complicated and usually not used.

For example, D may be at least 20", more particularly, at least 18" and even more particularly, at least 16". For the latter case, i.e. 16" membranes, the number n of membranes may be at least 10, more particularly, at least 8, and even more particularly, at least 5. For membranes of a larger diameter, for example 18", the number n of membranes may be at least 8, more particularly, at least 6, and more particularly, at least 4. The above examples refer to desalination membranes having a weight of about 80 Kg.

In particular, at a temperature difference of 15° C., thermal expansion effects may cause expansion of about 3 mm for each membrane. It is thus also appreciated that in a horizontal configuration, such an expansion can prevent proper closing of the PV, requiring applying pressure to the membrane or shortening portions of the conduits thereof, a process elegantly avoided by using the above suggested vertical arrangement.

The PVs may all be mounted on a horizontal base surface such that said longitudinal axis thereof is perpendicular to said horizontal base surface, i.e. is of a vertical orientation, allowing thereby loading and unloading of said membrane into said PV through the end of said PV remote from said horizontal base surface.

With the above design, it may be possible to provide simultaneous loading and unloading of a plurality of membranes into a single PV, and uniform access to each of the PVs, from the same height level.

Hereinafter, the end of said PV adjacent said horizontal base surface will be referred to as a 'bottom end' and the end remote from said horizontal base surface, i.e. the end through which loading and unloading is performed, will be referred to as a 'top end'. Said horizontal base surface will be referred to as 'bottom base surface'.

The bottom and top ends of said PVs may be adapted for connection to bottom and top pipeline grids for supplying said system with fluid to be desalinated, removing from said system permeate produced thereby, and brine.

Said bottom pipeline grid may be disposed on said bottom base surface, and said top pipeline grid may be disposed on a top base surface located above said bottom base surface. Thus, said bottom base surface may constitute a bottom service/maintenance platform at least for said bottom pipeline grid, and said top base surface may constitute a top service/maintenance platform at least for said top pipeline grid and for loading/unloading of said membranes.

It should be noted that several configurations of the pipeline grids may be used in the above system, for example, one of the following:
a) bottom pipeline grid may provide feed supply and front permeate removal, and top pipeline grid—brine and rear permeate removal;
b) bottom pipeline grid may provide brine and rear permeate removal, and top pipeline grid—feed supply and front permeate removal; and
c) a combination of the configurations (a) and (b) above, in which some of the PVs are connected according to the configuration (a) and some—according to configuration (b).

When a PV accommodates therein a plurality of membranes, each having a longitudinal axis, said membranes are stacked one on top of the other with the longitudinal axes thereof coinciding with the longitudinal axis of said PV.

According to a further aspect of the present invention there is therefore provided a membrane adapted to be received within a PV, said membrane comprising a main conduit, such as e.g. a permeate tube in a membrane, having a longitudinal axis defined therealong, a multi-layer membrane sheet wound around said main conduit, and an outer shell encapsulating said membrane sheet, wherein said outer shell is of such mechanical characteristics as to axially support, when located within said PV, most of the weight of a predetermined number of similar membranes stacked thereon.

With respect to the above aspect of the present invention and the pipeline grid arrangements previously discussed, it should be appreciated that when using the pipeline grid configuration (a), the upward flow of the fluid to be desalinated applies pressure to the membranes in an upward direction, which may effectively reduce load exerted on the outer shell of each membrane.

Alternatively, it should be appreciated that when using the pipeline grid configuration (b), the downward flow of the fluid to be desalinated applies pressure to the membranes in a downward direction, which may prevent displacement of the membranes within the PV during startup of the system, which may occur when using an upward flow.

According to yet another aspect of the present invention there is provided a membrane comprising a main conduit having a longitudinal axis defined therealong, wherein said main conduit is adapted to engagingly receive therein an anchoring arrangement for suspension of said desalination membrane in a vertical orientation for insertion into a vertically oriented PV.

According to a further aspect of the present invention there is provided an anchoring arrangement for suspension of a membrane having a central conduit of a diameter d, said anchoring arrangement comprising a central line with circumferential suspenders arranged therealong, wherein each of said suspenders is adapted to assume a first, retracted position in which the radial extension of each suspender about said line is of a diameter $d_1<d$, to allow insertion of the anchoring arrangement into said conduit in said retracted position, and a second, deployed position in which the radial extension of each suspender about said line is of a diameter $d_2>d$, to allow engagement between the suspenders and the central conduit's surface in said deployed position thereof.

Said anchoring arrangement may be in the form of a hooking mechanism, adapted to engage anchoring elements preformed in said main conduit for suspension of said membrane. For example, said conduit may be formed with recesses adapted to receive corresponding hooks of said anchoring arrangement. It would be appreciated that said anchoring elements should not interfere with the operation of said membrane.

Alternatively, said main conduit may have at least a layer of elastically deformable material, allowing deformation thereof without puncturing, and said anchoring arrangement may be formed with suspenders adapted to engage said deformable material by elastically deforming it to an extent sufficient to provide safe suspension of said membrane.

According to one particular design, said suspenders may be in the form of projections, such that the anchoring arrangement has a bee sting like shape. According to another particular design, said suspenders may be in the form of an attachment member formed with a central portion and at least two end portions disposed on opposite sides of said central portion, said attachment member being hingedly articulated to said central line, allowing it to assume a first, loose position in which it extends generally parallel to the central line, and a second, attachment position in which it extends generally transverse to said central line. When in said loose position, said attachment member is adapted for displacement within said main conduit, and when in said attachment position, said end portions are adapted to bear against the inner surface of said main conduit to thereby firmly engage the membrane.

According to a specific example, said anchoring arrangement may comprise at least one inflatable member adapted to assume a first, deflated position in which it may be inserted into said main conduit, and a second, inflated position, in which it is adapted to firmly engage the inner surface of the main conduit so as to allow anchoring said membrane, allowing, in turn, insertion/removal of said membrane into/from said PV cell.

Said at least one inflatable member may be made of a resilient material, adapted, in said inflated position to assume greater dimensions than those assumed thereby in said deflated position. In particular, the dimensions of the inflatable member during the inflated position may be greater than the diameter of the main conduit.

According to the above example, said inflatable member may be made of an impermeable material and be adapted to assume the inflated position due to introduction of a fluid (liquid or gas) material therein.

The anchoring arrangement according to the above example may comprise a single inflatable member extending 360° about said central line and therealong, such that the load exerted on the anchoring arrangement by the weight of the membrane is evenly distributed about the central line. Alternatively, said anchoring arrangement may comprise a plurality of inflatable members equally disposed about the central line and therealong so as to evenly distribute the load exerted on the central line.

According to yet another example, said anchoring arrangement may comprise a main body and a plurality of inflatable members, each being received within a groove formed in the main body. The inflatable members may be adapted for receiving air (or any other gas) from an external source.

According to still a further example, the anchoring arrangement may comprise a central line, and have pivot elements hingedly articulated to said central line, each pivot element having a first end and a second end and fitted at each of the first and the second ends with a pressure plate adapted to engage the conduit of the membrane.

The arrangement may be such that the pivot elements are articulated to the central line at a point which is offset from the center of the pivot element, i.e. the distance between the pivot point and the first end is greater than the distance between the pivot point and the second end. Thus, when the anchoring arrangement is vertically positioned, the asymmetry of the pivot elements may be adapted to bias the anchoring arrangement into the deployed position thereof.

The above anchoring arrangement may be provided with a trigger element adapted to bias the anchoring arrangement into the retracted position, thus allowing it to be inserted into said conduit.

When the membrane described above is assembled in a desalination system according to the first aspect of the invention, said membrane once suspended, may be brought to a desired location above the top end of a PV, such that the longitudinal axis of said membrane is aligned with the longitudinal axis of said PV. The membrane may then be lowered into said PV until it reaches its bottom end or abuts another membrane already located within said PV.

When used with a PV in a vertical orientation, the anchoring arrangement described above allows simultaneous inserting thereto or removal therefrom of a plurality of membranes. In particular, with a plurality of membranes stacked one on top of the other such that their main conduits are aligned with one another, said anchoring arrangement may be inserted into the main conduit of the top membrane and lowered, optionally through main conduits of further membranes, until it reaches the main conduit of a desired membrane, and engage the latter conduit, whereby a plurality of membranes may be suspended from the anchoring arrangement simultaneously. To allow this, the engagement is to be strong enough to bear the weight of said plurality of membranes.

According to a still further aspect of the present invention there is provided a two-stage anchoring arrangement adapted for removal of at least one desalination membrane from a top end of a vertically oriented PV, said anchoring arrangement comprising a first anchoring assembly adapted for fixed attachment to said PV, and a second anchoring assembly adapted for attachment to at least said one desalination membrane, wherein said second anchoring assembly is adapted to be vertically displaced, together with said desalination membrane, with respect to said first anchoring assembly, and said first anchoring assembly is adapted to be vertically displaced with respect to said PV, together with said second anchoring assembly and said desalination membrane.

Said first anchoring assembly may be adapted for mounting onto a rail system allowing it to displace therealong. Said second anchoring assembly may be generally similar to the anchoring arrangement described with respect to a previous aspect of the present invention.

A coupling may be provided between each two adjacent membranes adapted for sealingly connecting their adjacent ends in full alignment with each other.

According to one example, the coupling may be provided by a coupling unit disposed internally to the main conduits of the membranes, which may have a first portion which may be fitted into the conduit of one membrane and a second portion which may be fitted into the conduit of the adjacent membrane. According to another example, said coupling unit may be in the form of a fastener disposed externally to the main conduits of the membranes.

According to still another aspect of the present invention there is provided a desalination system comprising at least one PV having a longitudinal axis, adapted to receive two or more desalination membranes therein, and an optional coupling adapted to connect to adjacent desalination membranes, said system further comprising a plurality of sensors disposed along said longitudinal axis, wherein each of said plurality of sensors is located at least in one of said PV, one of said desalination membranes and the optional coupling, and wherein each of said plurality of sensors is adapted to measure at least one of the following:
  a) quality of a fluid passing through at least one of said two or more desalination membranes; and
  b) flow rate of a fluid passing through at least one of said two or more desalination membrane.

According to yet a further aspect of the present invention there is provided a coupling adapted to connect two adjacent desalination membranes, said coupling comprising at least one sensor adapted to measure at least one of the following:
  a) quality of a fluid passing through at least one of said membranes at the area of the coupling; and
  b) flow rate of a fluid passing through at least one of said membranes at the area of the coupling.

According to still a further aspect of the present invention there is provided a desalination membrane comprising at least one sensor adapted to measure at least one of the following:
  c) quality of a fluid passing through said membrane; and
  d) flow rate of a fluid passing through said membrane.

Said sensor may be operated continuously, measuring parameters throughout the operation of the desalination system. Alternatively, said sensor may be adapted to operate in bursts, sampling the above parameters along predetermined periods of time.

Said sensor may be adapted to be operated using an internal power source such as, for example, a battery, or an external source e.g. by electrical induction therefrom.

Said sensor may be adapted to transmit data produced based on the measurement taken thereby, to an outside source, for example a reader located outside said PV.

Said sensor may also be adapted for operation by said reader, wherein said reader may even be used as an external power source therefor. Said reader may be adapted for displacement between different sensors, for positioning thereof adjacent said sensor. In this case, when the reader is positioned adjacent said sensor, electrical induction between the two articles may cause the sensor to take a measurement and provide the data to said reader. Transfer of the data from said sensor to said reader may be performed in a wireless manner.

Said reader may be adapted for up and down displacement along a specific PV, on the outer side thereof, and be brought to locations aligned with different sensors, to allow any of its operations described above. To allow this mode of operation, a displacement mechanism may be provided, adapted for being displaced along a horizontal plane, which may be said top maintenance platform, and including a suspension device and cable having one end connected to said device and the other—to the reader for suspension thereof. The cable attaching the reader to said suspension device may be a data cable, and said device may be in turn connected, directly or wirelessly, to a Main Frame Computer (MFC), whereby all data collected by the reader may be transferred to said MFC.

In operation of the desalination system, said displacement mechanism is positioned above an array of vertically oriented PVs and, to collect a measurement from one of the sensors accommodated within one of the vertically disposed PVs, the following steps may be performed:

a) displacing said displacement mechanism along the horizontal plane to be located above the desired PV;

b) displacing said reader along the PV's vertical direction to be aligned with said sensor;

c) operating said sensor, possibly by the reader, to take the required measurement;

d) collecting data of said measurement by the reader; and e) transferring said data to the MFC.

In general, with respect to accessories such as the sensor, reader etc., the vertical orientation of the PVs may provide an easy manipulation of said accessories due to the vertical suspension, eliminating the need for intricate transport construction for horizontal displacement.

Data collected from various sensors may be used to perform an analysis of conditions of different membranes within different PVs. For example, the analysis of the data collected from all the membranes of a specific PV, may provide an indication of failure or malfunction in one of the membranes.

Once a faulty membrane has been detected it may be replaced. In order to replace such membrane in a PV, said anchoring arrangement, in a retracted position, may be inserted from the top end of the PV, into the main conduit of the membrane, possibly, having passed through main conduits of preceding membranes, i.e. membranes disposed closer to the top end of the PV than the damaged membrane. It may then proceed to assume its deployed position, to securely engage said damaged membrane and, optionally, all the preceding membranes stacked thereon, and may be raised, carrying said faulty membrane along with all of the preceding membranes positioned stacked thereon.

The faulty membrane may then be displaced to a location outside the PV to rest on a surface, for example, said bottom maintenance surface, where said anchoring arrangement may disengage therefrom and proceed with picking up a replacement membrane to be inserted into said PV.

In case only the faulty membrane has been removed from the PV, i.e. having not additional membranes stacked thereon, the anchoring arrangement may assume a retracted position, and be withdrawn upwards from the main conduit of said damaged membrane.

In case said faulty membrane had stacked thereon a number of additional membranes, said anchoring arrangement may assume a retracted position in which it is withdrawn from the main conduit only of the faulty membrane, i.e. still being received within the main conduits of all preceding membranes. Once withdrawn, said anchoring arrangement may re-assume a deployed position, and thereby engage at least the bottom most preceding membrane, i.e. the membrane positioned directly above said damaged membrane. In this position, all of said preceding membranes may be suspended, and re-introduced into said PV.

Upon re-introduction of said preceding membranes into said PV, said anchoring arrangement may further proceed with picking up a replacement membrane to replace said faulty membrane, and placing it on top of said preceding membranes within said PV. Alternatively, said anchoring arrangement may first insert a new membrane into said PV, and only then re-introduce said preceding membranes into said PV as previously described.

According to still another aspect of the present invention there is provided a method for monitoring conditions of a plurality of desalination membranes in a PV, comprising: providing said membranes with sensors as described above, receiving input data collected from said sensors, analyzing said data and providing output data indicative of said conditions for at least one of said membranes.

Said analysis may include normalization of values measured by at least one sensor so as to display a qualitative graph of the membrane conditions, in the form allowing alerting the operator of a possible malfunction without requiring the operator's knowledge of said values.

The above method may allow, inter alia near real-time membrane malfunction detection, exact pin-pointing of faulty membranes, and an accurate, cost-effective measurement.

According to still a further aspect of the present invention there is provided a desalination system comprising:

a) an array of vertically disposed PVs, each PV accommodating one or more desalination membranes;

b) a pipeline grid adapted for conducting fluid to be desalinated to said PVs and produced permeate from said PVs;

c) a plurality of sensors disposed along the longitudinal axis of each PV, adapted to measure flow rate and/or quality of fluid passing through said one or more membranes; and d) a reader connected to an MFC adapted to be displaced along said PV, to be aligned with at least one of said plurality of sensors, to receive data therefrom.

Said system may be completely automated and controlled by the MFC, removing the need for human personnel to perform measurements, replacement of membranes, etc. For example, each PV and each membrane therein may have their own index number recognizable by the MFC, whereby, upon detection of a damaged membrane, replacement of a membrane is performed as follows:

a) the MFC receives the index number of the PV and the membrane required to be replaced;

b) a command is given to the anchoring arrangement (also connected and controlled by the MFC) to move to a position above said PV; and c) said membrane is replaced as previously described.

Said system may further be adapted for automatically performing the method of monitoring conditions of a plurality of desalination membranes in the PVs, as described above, whereby even detection of damaged membranes may be achieved in an automated fashion.

According to a still further aspect of the present invention, there is provided a desalination system comprising at least one row of PVs, each having a feed inlet at a first end thereof and a brine outlet at a second end thereof and containing at least one desalination membrane, said PV being adapted for passage of fluid to be desalinated between said first and said second end, wherein said feed inlet is fitted with a first sensor adapted for acquiring a first set of parameters of a test substance introduced into said fluid and passing therealong inside the PV, and said brine outlet is fitted with a second sensor adapted for acquiring a second set of parameters of the test substance.

The acquired sets of parameters may be used in diagnosis of parameters of the fluid flowing through said PV from said fluid inlet to said fluid outlet.

In particular, said first sensor and said second sensor may be adapted both for detecting the presence of said test substance and for detecting the concentration thereof. Thus, each sensor may provide two parameters: C—concentration of the test substance and t, the time the test substance was detected, thus yielding four parameters altogether. These parameters may be used for determining flow rate within each of the PVs. Exact formulas and explanations will be discussed in the detailed description.

It is also appreciated that using the test substance for determining flow rate within the PVs, eliminates the need for complicated and costly flow meters. In addition, flow meters are generally equipped at a distal end of a main feed line, providing the feed for the entire row of PVs, and there is required a predetermined length of the main feed line before and after the location of the flow meter, before entering the row of PVs, in order to allow accurate measurement of the flow rate (e.g. for a feed line of diameter D, there is required a length equal to 2D before the flow meter and 5D after the flow meter to eliminate turbulence effects). Thus, using a test substance as suggested above, may effectively shorten the overall length of a row of PVs, thus contributing to a more compact and space-efficient arrangement of the PVs in the desalination system.

According to a still further aspect of the present invention there is provided a desalination system comprising at least one common feed line having a first end and a second end, and at least one row of PVs arranged along said common feed line, each PV having a feed inlet at a first end thereof in fluid communication with said common feed line, and a brine outlet at a second end thereof, and containing at least one desalination membrane, each PV being adapted for passage of fluid to be desalinated between said first and said second end, wherein feed fluid is introduced into said common feed line from both said first and said second end thereof, i.e. said common feed line having a double-sided feed.

It should be appreciated that when using a double-sided feed, the diameter of the common feed line may be reduced in half with respect to a common feed line having a one-sided feed. Reducing the diameter of the common feed line may allow closer spacing between two adjacent rows of PVs, thus further contributing to a more compact and space-efficient arrangement of the PVs in the desalination system.

According to still a further aspect of the present invention there is provided a desalination facility comprising a structure having a roof, and adapted to be accommodated therein at least one PV having a distal end and a proximal end and a length L therebetween, and oriented such that said distal end is closer to said roof than said proximal end, wherein said PV is adapted for receiving at least one desalination membrane, loaded therein or unloaded therefrom via said distal end, and wherein there extends a distance M between said distal end and a roof portion located above said distal end, such that $M \leq L$.

Said at least one desalination membrane may be loaded/unloaded into/from said PV using an anchoring arrangement adapted for engaging said desalination membrane and displacing to/from said distal end, and said roof may be an adjustable roof designed such that at least a roof portion thereof located above said distal end is adapted to open so as to allow said anchoring arrangement to pass therethrough during said loading/unloading.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2 illustrates one example of a conventional RO membrane used in the system shown in FIG. 1;

FIGS. 4C and 4D are schematic cross-sectional views of one example of a membrane with an anchoring arrangement within it, according to the present invention, in a retracted and a deployed position respectively;

DETAILED DESCRIPTION OF EMBODIMENTS

Figure 1:
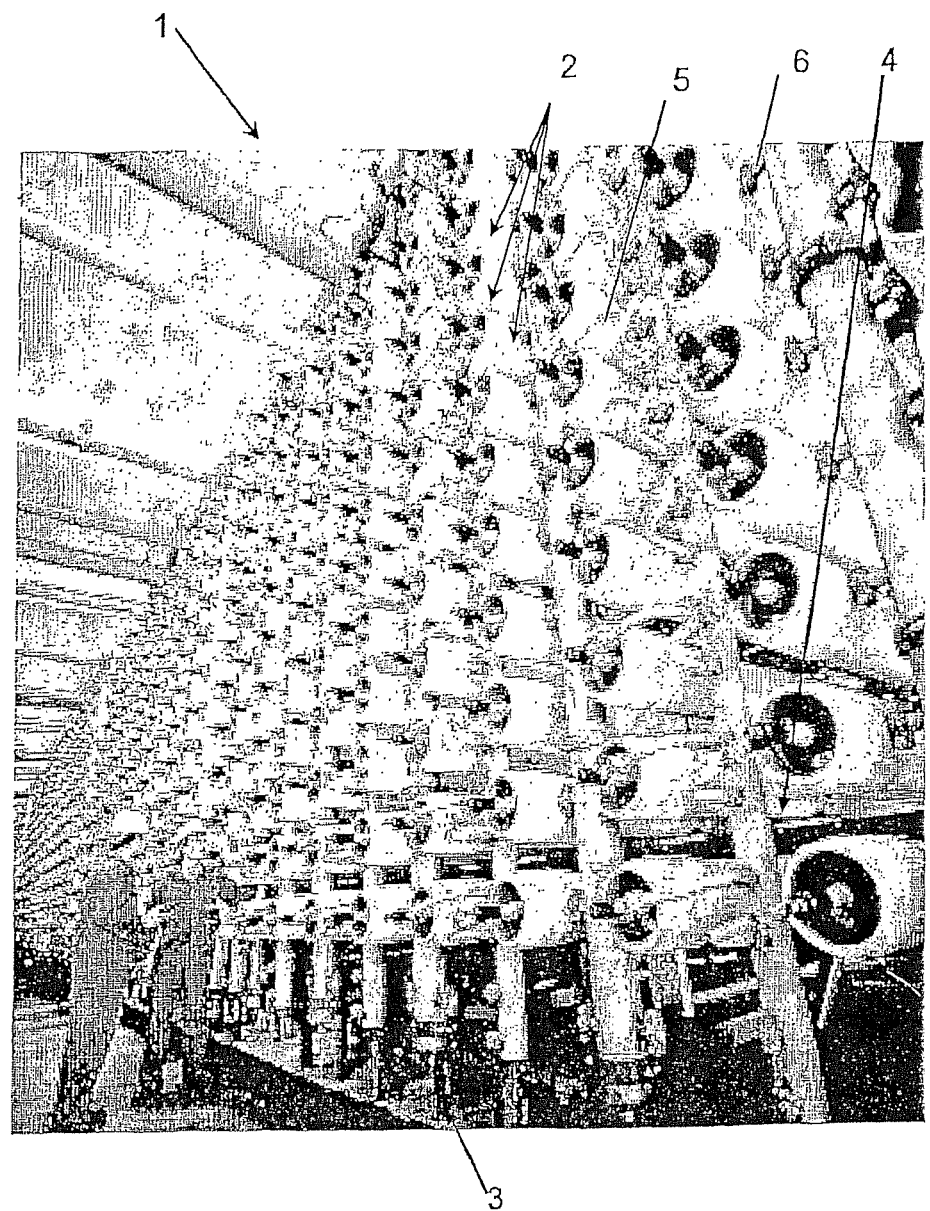
FIG. 1 illustrates a known RO desalination system with a plurality of horizontally mounted pressure vessels (PVs)
Figure 3A:
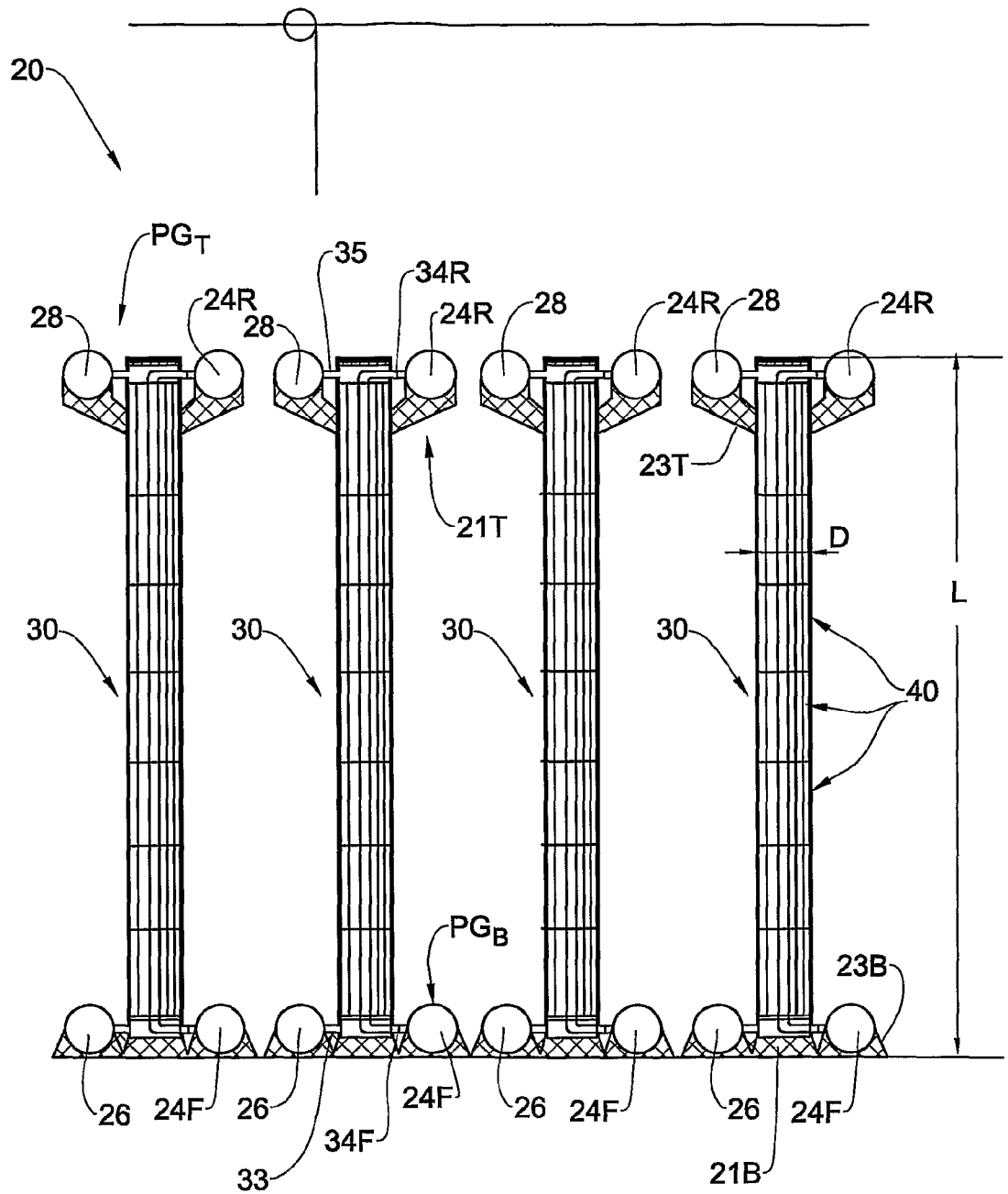
FIG. 3A is a schematic cross-sectional view of one example of a desalination system according to the present invention.
Figure 3B:
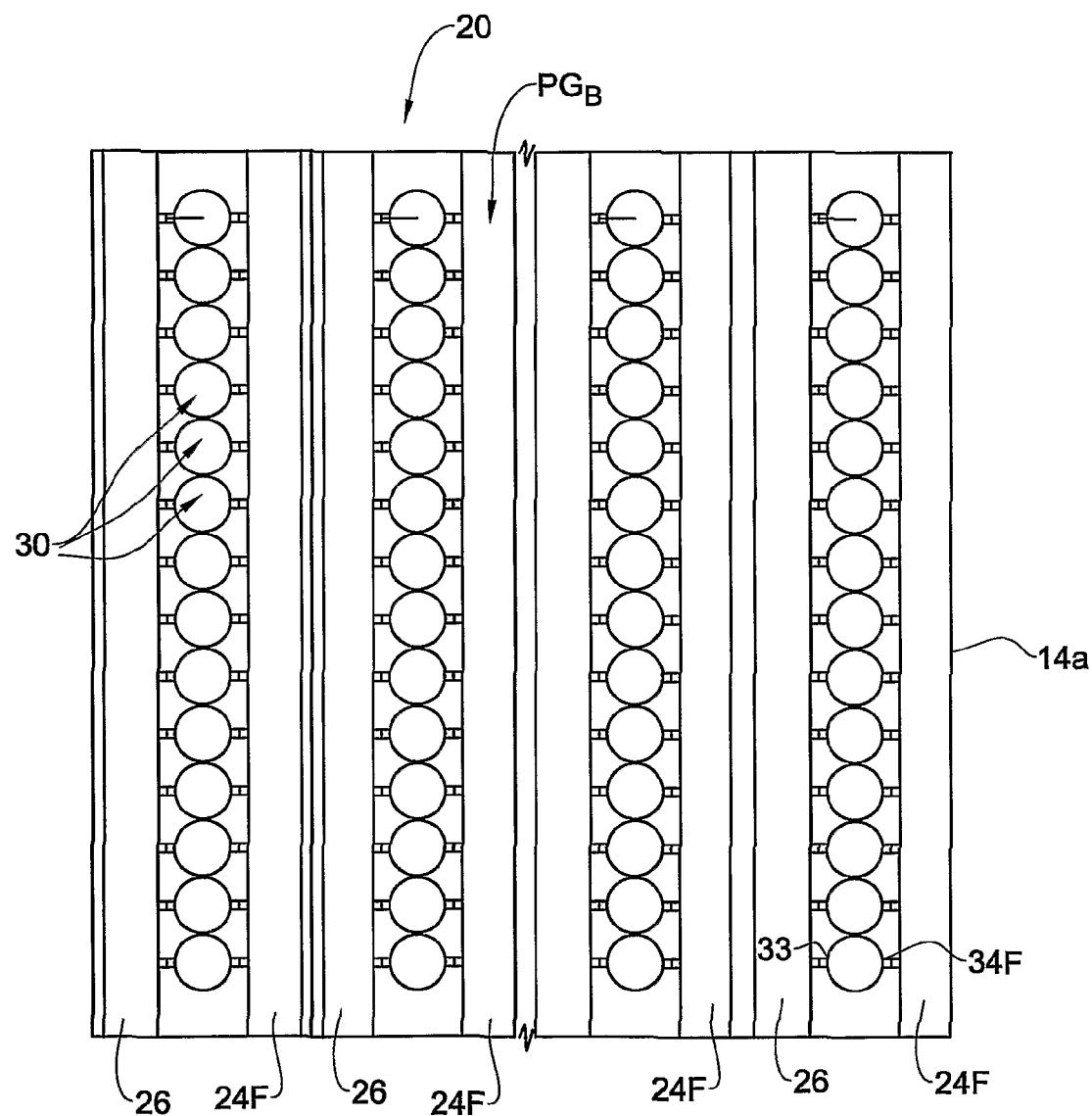
FIG. 3B is a schematic top view of the desalination system shown in FIG. 3A.

FIGS. 3A and 3B show one example of a desalination system according to the present invention, which is a reverse osmosis (RO) desalination system generally designated 20, comprising a plurality of pressure vessels (PVs) 30 mounted vertically on a base platform constituting a bottom base surface 21B and having a common top base surface 21T.

Each PV 30 comprises a plurality of RO desalination membranes 40, stacked one on top of the other so that they are fully aligned.

Each membrane 40 is of a construction similar to that of the known membrane 10 shown in FIG. 2 and described in the Background of Invention. In particular, with reference to FIGS. 4C and 4D, the membrane 40 comprises a permeate tube 42 having a central axis X and a diameter $D_P$, a membrane core 44 wound on the permeate tube 42, and an outer shell 46. However, the membrane 40 according to the present invention may have some specific features particularly suitable for the vertical disposition of the PVs, as will be explained in detail later.

The bottom base surface 21B and the top base surface 21T have thereon respective bottom and top pipeline grids $PG_B$ and $PG_T$. The bottom pipeline grid $PG_B$ includes a feed line 26 and a front permeate line 24F, and the top pipeline grid $PG_T$ includes a rear permeate line 24Ra and brine line 28.

Each PV 30 has an essentially cylindrical body 32 having a diameter D ranging between about 8" and 16". The PV body 32 has bottom end 32B, formed with a feed inlet port 33, front permeate outlet port 34F, and a top end 32T formed with a brine outlet port 35 and rear permeate outlet port 34R. The PV 30 is fitted with a removable cover 31 at its top end 30T, in which at least the rear permeate outlet port 34R is formed as better seen in FIG. 4A.

In assembly, the PVs 30 are positioned on the bottom base surface 21B vertically such that the feed inlet port 33 and the front permeate outlet port 34F are connected to the feed and front permeate lines 26, 24F respectively, and the brine outlet port 35 and rear permeate outlet port 34R are connected to the concentrate and rear permeate lines 24R, 28 respectively, on the top base surface 21T. To align the above lines of the bottom and top pipeline grids with the corresponding ports of the PVs, the bottom base surface 21B and the top base surface 21T are formed with support channels 23B and 23T in which these lines are received.

With further reference to FIG. 3B, the PVs 30 are arranged in a plurality of rows having, mounted therebetween on the bottom base surface 21B, with the front permeate and feed lines 24F, 26 extending parallel to one another and parallel to the bottom base surface 21B. The rows of PVs 30 are sufficiently spaced from one another to allow an operator or a maintenance person to pass therebetween and attend to any maintenance issues such as malfunctions, routine checks etc. Therefore, the bottom base surface 21B constitutes a bottom maintenance surface for attending the bottom pipeline grid $PG_B$ and the top base surface 21T constitutes a top maintenance surface for attending the top pipeline grid $PG_B$, and the membranes 40.

It should however be appreciated that the above pipeline grid arrangement may be such that the inlet ports are located at the top end of the PV 30 and the outlet ports are located at the bottom end of the PV, such that the flow within the PVs is only in a downward direction. Such an arrangement may prevent displacement of membranes within the PV during the beginning of the PV's operation (i.e. fluid pushing the membranes in an upward direction), which tends to happen when using an upward flow.

Figures 4A, 4B:
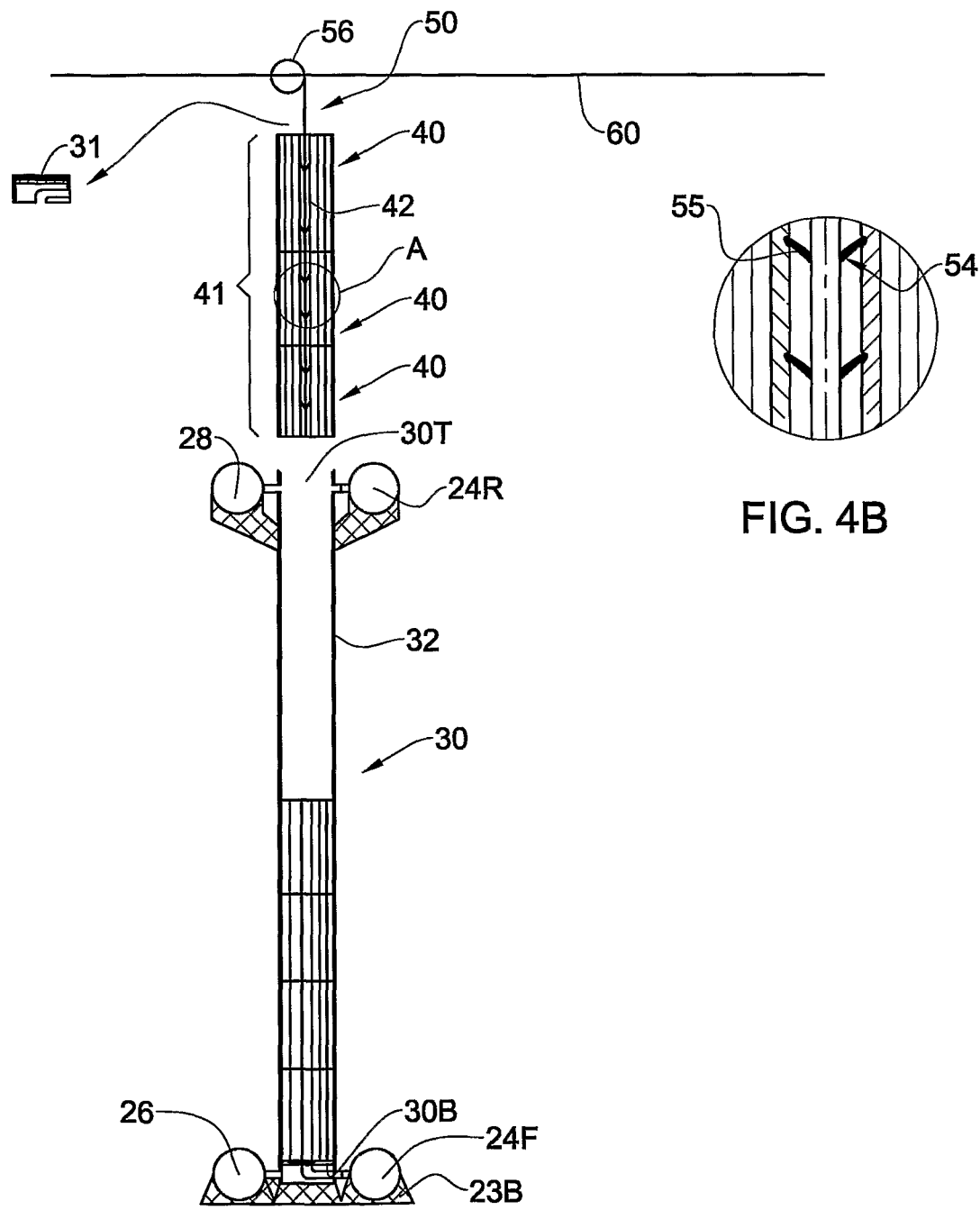
FIG. 4A is a schematic cross-sectional view of a single PV used in the desalination system shown in FIGS. 3A and 3B, with a plurality of membranes.
FIG. 4B is an enlarged view of detail 'A' in FIG. 4A.

Turning now to FIG. 4A, the PV 30 is shown in a loading/unloading position, in which a group 41 of the membranes 40 is located outside the PV either prior to being loaded therein or after having been unloaded therefrom. In this position, the cover 31 is removed from the PV 30. An anchoring arrangement 50 displaceable along an anchoring line 60 is shown suspending the group 41 of the membranes 40 in the above described position. It should be noted that loading and unloading the membranes 40 from the top end 30T allows simultaneous insertion of a plurality of membranes 40 into the PV 30. However, if desired the same anchoring arrangement 50 may be used to load/unload the membranes one by one.

One possible design of the anchoring arrangement 50 is shown in FIGS. 4C and 4D. The anchoring arrangement 50 shown in these Figures comprises a central line 52, and circumferential suspenders 54 arranged therealong, each being formed with several membrane engaging elements 55 whose tips 57 may protrude from the central line 52 to a minimal extent (FIG. 4C) in which the suspender 54 is in its retracted position and has a diameter $d_1$, and to a maximal extent (FIG. 4D) in which the suspender 54 is in its deployed position and has a diameter $d_2$.

In the retracted position, the membrane engaging elements 55 of each suspender 54 are oriented approximately axially, i.e. along the central line 52, whereby the tips 57 thereof define a diameter $d_1 < D_p$ of the suspender 54 about the central line 52, where $D_p$ is the diameter of the permeate tube 42 of the membrane 40. In this position, the anchoring arrangement 50 is freely displaceable along the permeate tube 42 of the membrane 40. In the deployed position, the membrane engaging elements 55 of each suspender 54 are oriented approximately radially, i.e. transverse to the central line 52, whereby the tips 57 thereof define a diameter $d_2 > D_p$ of the suspender 54 about the central line 52. In this position, the tips 57 of the elements 55 of each suspender 54 deform the permeate tube 42 of the membrane 40.

The anchoring arrangement 50 or any alternative anchoring arrangement has to be designed so as engage the permeate tube 42 of the membrane 40 without damaging it. In this connection, it should be mentioned that, for use with the anchoring arrangement shown in FIGS. 4C and 4D, the permeate tube 42 should be made of a deformable resilient material, allowing the suspenders to sink therein without puncturing it. Such a material may be for example FRP, PVC, PP.

It should be appreciated that according to other possible designs, the permeate tube 42 may be preformed with recesses or indentations adapted to receive the tips 57 of the elements 55.

The anchoring arrangement 50 further comprises an anchoring module 56 attached in a displaceable manner to the anchoring line 60, and may also be equipped with a crane, monorail etc for raising and lowering the central line 52 with the membrane or several membranes 40 carried thereby.

In operation, in order to suspend a membrane 40, the anchoring arrangement 50 is first displaced along the anchoring line 60 to a location where it is positioned above the membrane 40, i.e. to a position in which the central line 52 of the anchoring arrangement is aligned with the central axis X of the permeate tube 42 of the membrane 10. Thereafter, the central line 52 with the suspenders 54 in their retracted position is lowered by the anchoring module 56 until the portion of the central line 52 with the suspenders 54 is received within the permeate tube 42 of the membrane 40 (shown FIG. 4C). Once the portion of the central line 52 is received within the permeate tube 42, the suspenders 54 assume their deployed position, in which their membrane engaging elements 55 sink into the permeate tube 42, thereby being securely engaged therewith (shown FIG. 4D). In this position, the membrane 40 may be suspended and displaced to a desired location.

It is thus clear that the above described arrangement allows simultaneous suspension of a plurality of membranes 40, as shown in FIG. 4A, which in turn, allows fully loading a single PV 30 with membranes in one operation, and similar unloading of such membranes, e.g. when it is desired to replace a faulty membrane which is not the uppermost membrane in the PV. For a group of membranes 40 stacked one on another to be simultaneously loaded into, or unloaded from, a PV 30, the suspenders 54 may engage the permeate tubes of one of the following:
 all the membranes 40 of the stack;
 only some of the membranes 40 of the stack, including the lowermost membrane; and even
 only the lowermost membrane 40 of the stack.

In order to replace a faulty membrane in a PV, first, the PV 30 assumes a loading/unloading position (shown FIG. 4A) by removing the cover 31 thereof. Thereafter, the anchoring arrangement 50 is displaced horizontally along the anchoring line 60 to be positioned directly above the PV 30. Once in position, the central line 52 of the anchoring arrangement 50, with the suspenders 54 in the retracted position (shown FIG. 4C) is inserted into the permeate tubes 42 of the preceding membranes (those disposed above the faulty membrane), until it is received within the permeate tube 42 of the faulty membrane. The suspenders 54 of the anchoring arrangement 50 then proceed to assume the deployed position (shown FIG. 4C) whereby the suspenders 54 securely engage the permeate tubes 42 of the faulty membrane and, if desired, all or a part of its preceding membranes.

Once securely engaged, the central line 52 is raised along with the membranes 40 suspended therefrom until the membranes are removed from the PV 30. Once removed, the anchoring arrangement 50 and membranes 40 may be displaced along the anchoring line 60 so as to bring the anchoring arrangement 50 and membranes 40, for example, above a repair platform (not shown). Thereafter, the central line 52 with the membranes is again lowered such that the faulty membrane rests on the repair platform.

In this position of the membranes 40, the suspenders 54 of the anchoring arrangement 50 re-assume a retracted position, and the central line 52 is slightly raised so as to be removed from the faulty membrane, i.e. being received only within the permeate tubes 42 of the preceding membranes. Thereafter, the suspenders 54 may re-assume a deployed position so as to securely engage the permeate tubes 42 of the preceding membranes. The preceding membranes may then be returned to the PV 30 in a similar manner.

The preceding membranes may be first returned to the PV 30 and thereafter a new membrane 40 is inserted into the PV on top of the preceding membranes. Alternatively, the new membrane may first be inserted into the PV 30, and only then are the preceding membranes positioned on top of the new membrane.

Once the membranes 40 have been re-introduced in the PV 30, the top cover 31 is be placed back on top of the PV 30, thereby bringing the PV to its working position.

In this respect, it should be noted that it is often the case that when a membrane is positioned within the PV for an extensive amount of time, chemical residue, scaling fouling and other materials accumulate between the outer shell of the membrane and the inner surface of the PV, thereby causing the desalination membrane to become 'lodged' within the PV, i.e. of low susceptibility for changing its position along the longitudinal axis of the PV. Thus, when attempting to remove such a desalination membrane, it is first required to release the membrane from its 'lodged' position before removing it from the PV.

The loads exerted on the anchoring arrangement 50 during such 'unlodging' of the desalination membrane are far greater than the loads exerted thereon during suspension of the membrane. One possible solution for this problem would be the use of a more robust anchoring arrangement and crane, capable of withstanding the loads applied thereto during 'unlodging'. However, it is appreciated that such a solution would be an 'over-design' since the 'unlodging' operation only takes up a brief amount of time with respect to the entire time required for the loading/unloading operation.

Figure 7A:
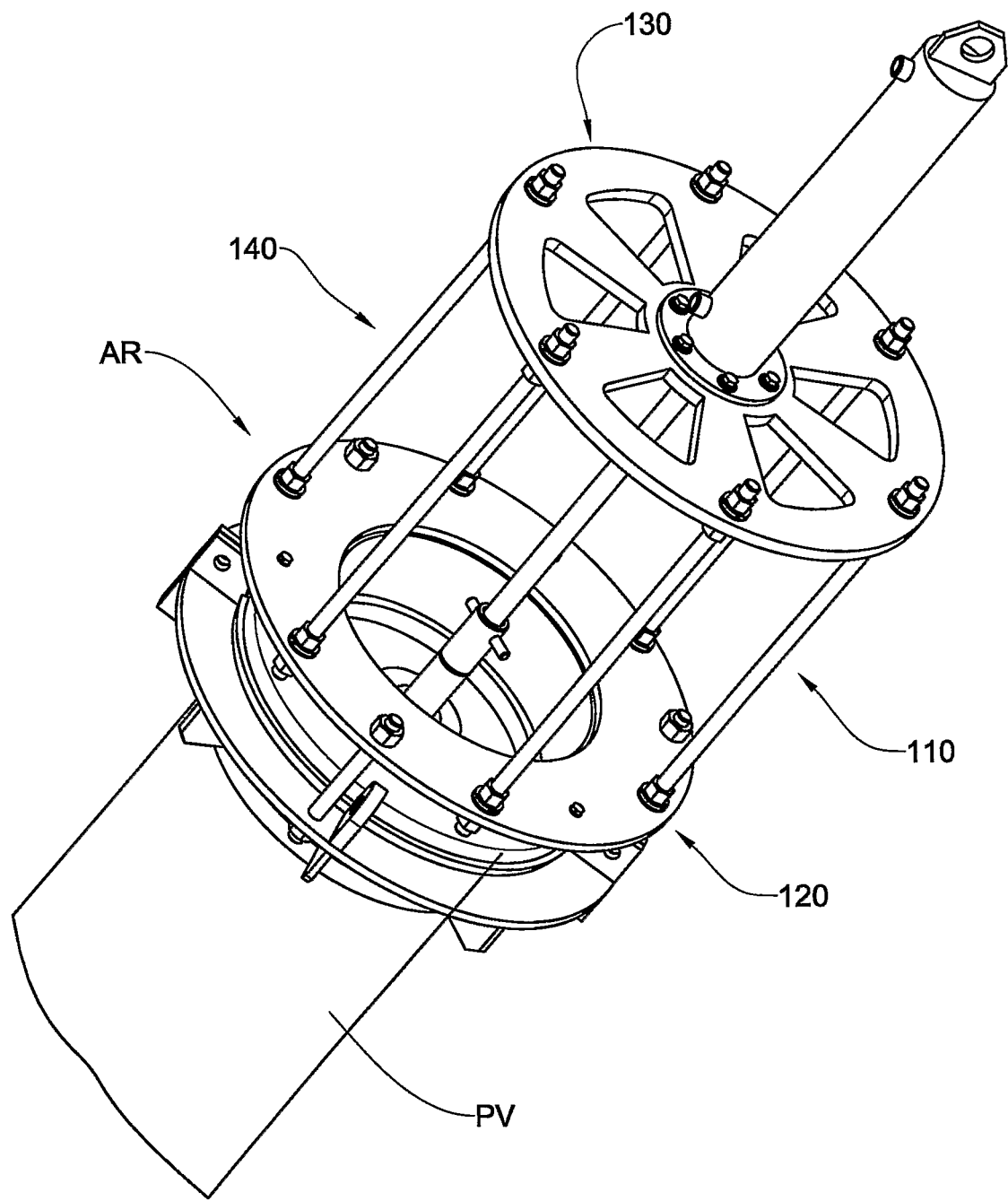
FIG. 7A is a schematic isometric view of an anchoring arrangement according to another aspect of the present invention, when attached to a PV cell.
Figure 7B:
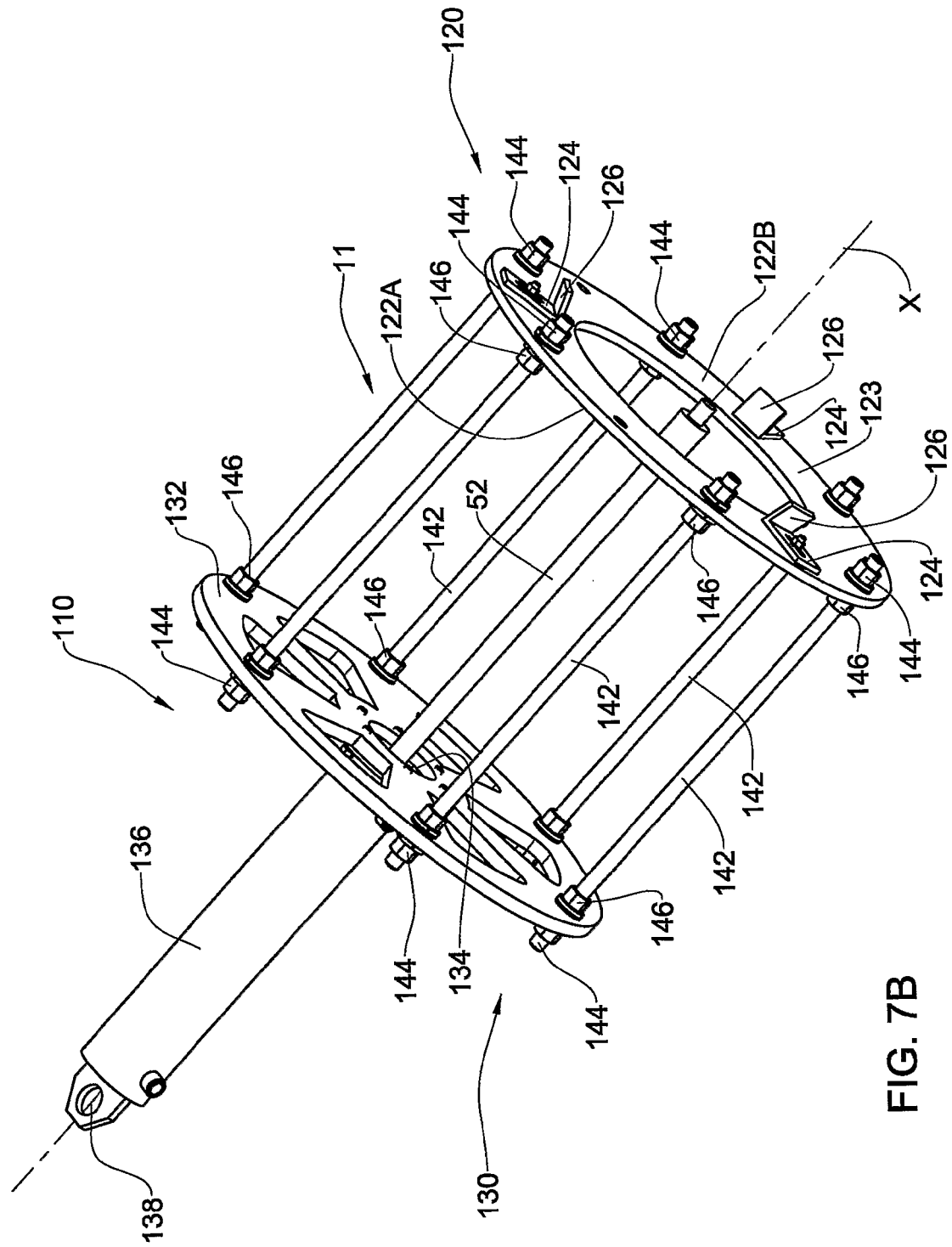
FIG. 7B is a schematic bottom isometric view of the anchoring arrangement shown in FIG. 7A.
Figure 7C:
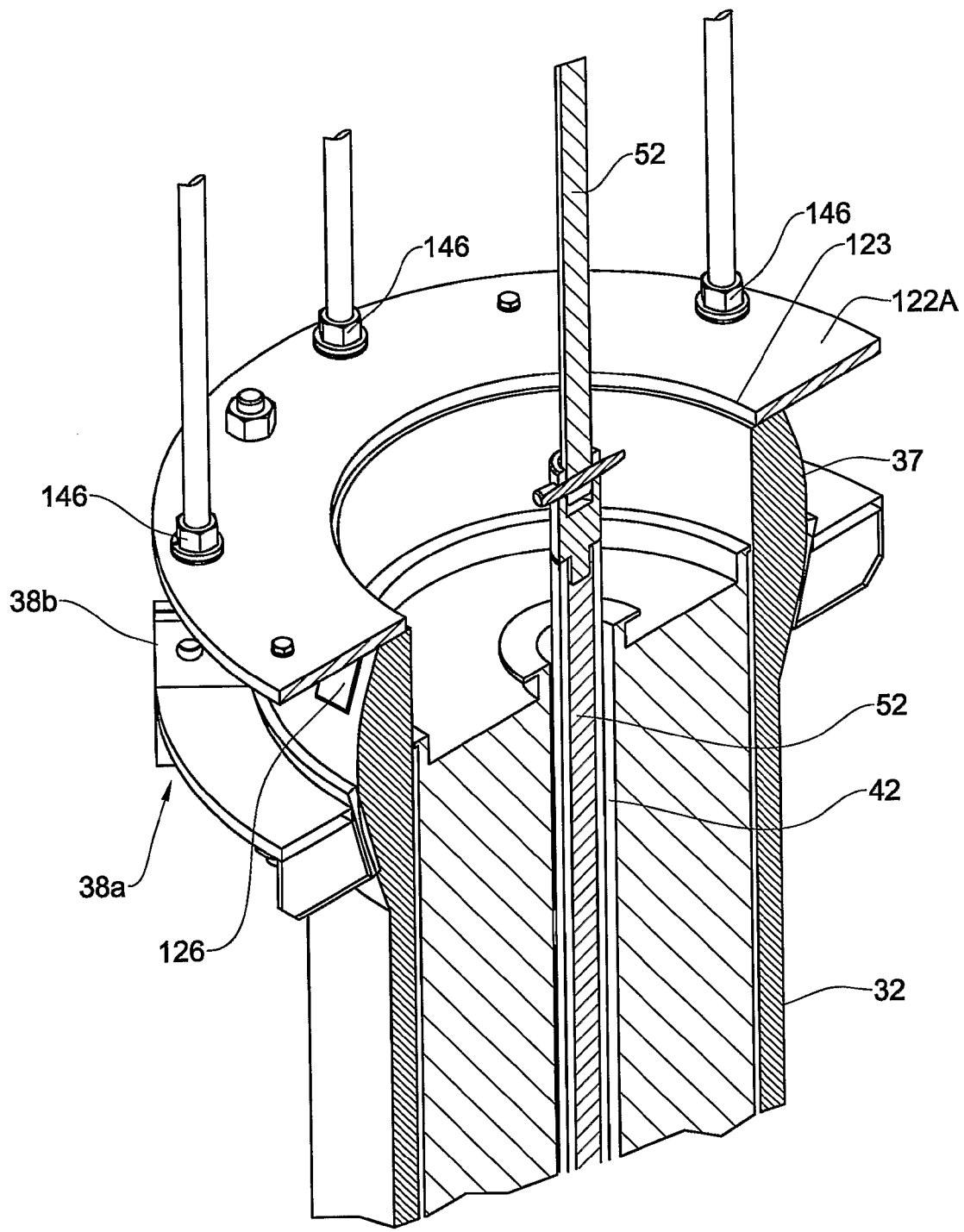
FIG. 7C is a schematic isometric cross-section view of the anchoring arrangement shown in FIG. 7A.

Another solution is shown with reference to FIGS. 7A to 7C, in which a two-stage anchoring arrangement generally designated AR adapted for the removal of one or more membranes from the PV is shown comprising a first-stage anchoring assembly generally designated 110 and a second-stage anchoring assembly constituted by the previously disclosed anchoring arrangement 50, of which only the central line 52 is shown.

The two-stage anchoring arrangement is designed such that at a first-stage of unloading the first-stage assembly 110 releases the desalination membrane from its 'lodged' position, whereas at a second-stage of unloading, the anchoring arrangement 50 previously described proceeds with the suspension and displacement of the desalination membrane to a desired location.

The first-stage anchoring assembly 110 comprises a PV attachment section 120 adapted for attachment to a distal end of a PV, and a second-stage attachment section 130 adapted for attachment to the second-stage anchoring assembly 50. The sections 120, 130 are spaced apart by a spacing array 140, adapted to provide a desalination membrane with sufficient space to displace in during the first stage of unloading.

It should also be appreciated that this space is primarily useful when the PV is fully stacked with desalination membranes, i.e. the desalination membranes take up all the space within the PV. In other words, the desalination membrane positioned closest to the PV end through which unloading is performed, is located at the distal end itself. Thus, it should also be understood that for a PV which is not fully stacked, the first and second sections 120, 130 may be used without the spacing array 140.

The PV attachment section 120 is formed with a circular disc 122 formed with a central opening 121, and having an anchoring face 122a and a PV face 122b, such that when the first-stage anchoring assembly 110 is mounted onto the PV 30, the anchoring face 122a faces the second-stage anchoring section 130, and the PV face 122b faces the distal end of the PV. The PV face 122b of the circular disc 122 has a contact area 123 adapted for coming in contact with a lip 39 (shown FIG. 7C) of the distal end of the PV 30 when mounted thereon.

The PV attachment section 120 further comprises three centering elements 124 attached to the PV face 122b, each being formed with an inclined portion adapted to come in contact with an outer surface 32 of the PV 30. The centering elements 124 are equally disposed about the central axis X of the circular disc 122 (i.e. at 120° intervals) to thereby allow the first-stage anchoring assembly 120 to become aligned with the PV, i.e. such that the central axis X of the circular disc is aligned with the longitudinal axis of the PV 30.

The second-stage attachment section 130 is also formed with a circular disc 132 formed with a central opening 134, and further comprising an anchoring piston 136 attached to an anchoring line 137 adapted for attachment to the second-stage anchoring assembly 50. The anchoring piston 136 further comprises a lifting eye 138 adapted for attachment to a main crane (not shown), which is in turn adapted to displace the entire anchoring arrangement from the PV 30.

The spacing array 140 comprises a plurality of spacing rods 142 extending between a peripheral portion of the circular disc 122 of the PV attachment section 120 and a corresponding peripheral portion of the circular disc 132 of the second-stage anchoring attachment section 130. Each of the spacing rods 142 is secured in place using nuts 144 and 146.

With particular reference to FIG. 7C, it is observed that the PV 30 is formed with a thickened top end 37 and has an upper lip 39, such that when positioned on the top end of the PV 30, the contact area 123 of the PV face 122 is flush against the lip 39 of the PV's top end, and the inclined portions 126 of the centering elements 126 are flush against the outer surface of the PV's top end.

The arrangement is such that when the second-stage anchoring assembly 50 is attached to the anchoring line 137, activation of the piston 136 entails withdrawal of the central line 52 from the PV and in turn of the entire second-stage anchoring assembly 52, thus disengaging the membrane/s from their 'lodged' position within the PV 30. It is appreciated that the great loads required for 'unlodging' the membrane are now taken not by the main crane (not shown) but by the construction of the first-stage anchoring assembly 110, by using the PV 30 itself as fulcrum, in a manner similar to the operation of a cork-screw.

Once the membrane/s is 'unlodged' and is able to freely slide within the PV, the main crane lifts the first-stage anchoring assembly 110 using the lifting eye 138, along with the second-stage anchoring assembly and the suspended membrane/s, to displace the membrane/s to a desired location.

With reference to FIGS. 8A to 8G, the second-stage anchoring assembly may be of various designs, and not limited to the previously disclosed design of the anchoring arrangement 50.

Figure 8A:
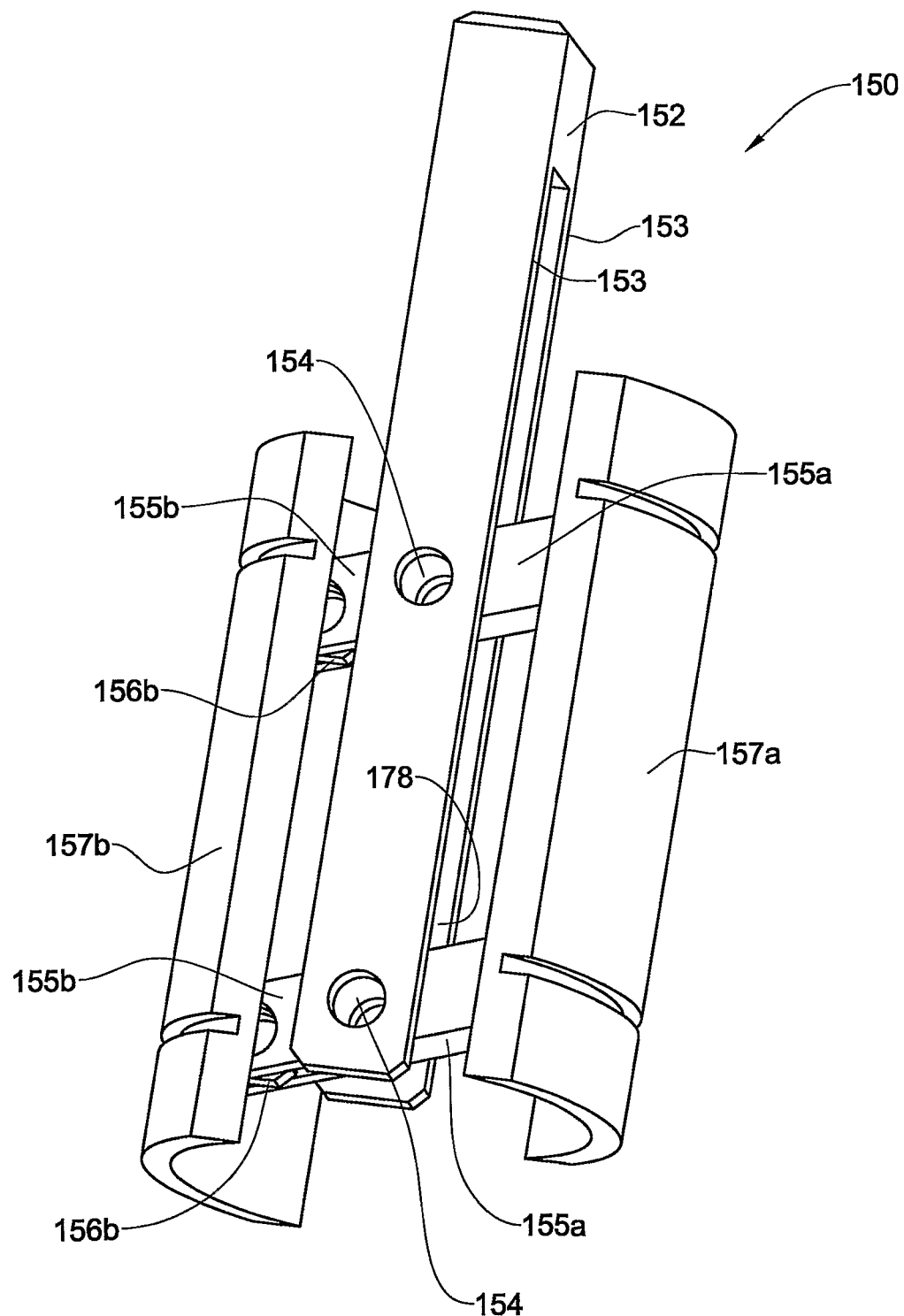
FIG. 8A is a schematic isometric view of a first embodiment of an anchoring assembly used in the anchoring arrangement shown in FIGS. 7A to 7C.
Figure 8B:
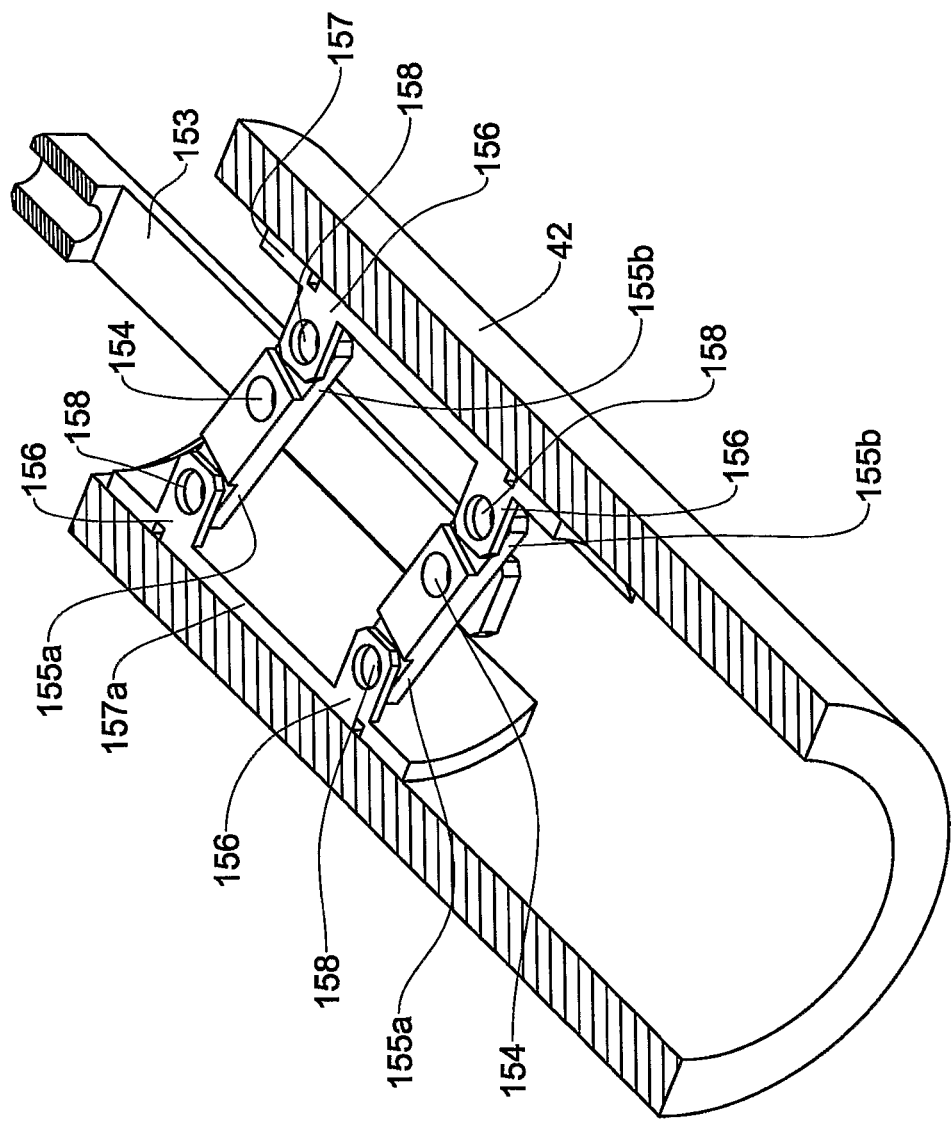
FIG. 8B is a schematic isometric cross-section view of the anchoring assembly shown in FIG. 8B when inserted into a conduit of a membrane to be anchored thereby.

With particular reference to FIGS. 8A and 8B, another design of a second-stage anchoring arrangement is shown generally designated as 150, and comprising a central line 152, pivot elements 155 adapted to pivot thereabout, and pressure plates 157 adapted to engage the inner surface of the main conduit 42 of the membrane 40.

The central line 152 is formed with two fork portions 153 with a gap extending therebetween. Within the gap, several pivot elements 155 (in the present example only two pivot elements are shown) are pivotally hinged via pivot points 154. It is observed that the pivot point 154 is not located at the middle of the pivot element 155, but rather is offset to form two asymmetric portions—155a and 155b, 155a being slightly longer than the latter.

The pivot elements 155 are fitted with pressure plates 157 which are pivotally attached to each portion 155a, 155b via a hinge 158 formed in a slat 156 projecting from the pressure plate 157.

The arrangement is such that the second-stage anchoring assembly 150 may assume a first, retracted position in which the pivot elements 155 extend generally parallel to the central line 152, whereby the assembly 150 may be inserted into the main conduit 42 of the membrane 40, and a second, deployed position, in which the pivot elements 155 are generally transverse to the central line 152 such that the pressure plates 157 come in contact with the inner surface of the main conduit 42 to apply to pressure thereto. The pressure on the inner surface of the membrane's conduit 42 should be sufficient so as to allow suspension of the membrane 40.

The anchoring arrangement 150 may be biased, due to gravitational forces into its deployed position, since the portion 155a overweighs the portion 155b, operating in a manner similar to a parallelogram mechanism. Thus, the transfer from the deployed position to the retracted position is achieved using a trigger element (not shown) which may be in the form of an electric motor, a pulling rod or the like.

In operation, the second-stage anchoring assembly 152 is inserted into the main conduit 42 in its retracted position until it reaches the desired membrane/location. Thereafter, the operation of the trigger element is halted, allowing the anchoring arrangement 150 to displace, due to gravitational forces, to its deployed position such that the pressure plates 157 are flush against the inner surface of the main conduit 42. In this position, since the portions 155a and 155b are not of equal length, pulling on the central line 152 will cause the pivot elements 155 to pivot about the pivot point 154, biasing them further towards the deployed position, thus increasing the pressure applied to the inner surface of the main conduit and providing firmer engagement between the anchoring assembly 150 and the desalination membrane 40.

Figure 8C:
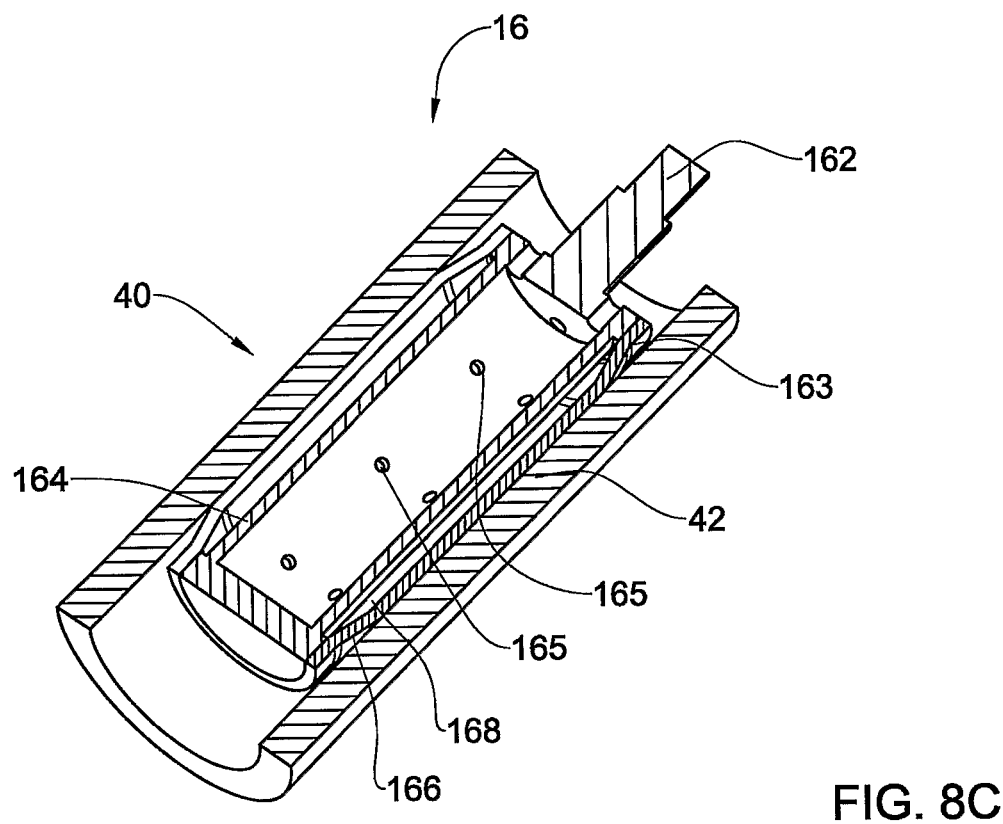
FIG. 8C is a schematic isometric cross-section view of a second embodiment of an anchoring assembly used in the anchoring arrangement shown in FIGS. 7A to 7C, when inserted into a conduit of a membrane to be anchored thereby.

Turning now to FIG. 8C, a further design of the second-stage anchoring assembly is shown generally designated as 160 and comprising a central line 162, a main chamber 164, and a peripheral inflatable portion 166.

The central line 162 is formed with an air inlet 163 adapted to provide air to the main chamber 164, which is in turn formed with a plurality of discharge apertures 165 adapted to deliver the air into the peripheral inflatable portion 166 made of an impermeable material.

The anchoring assembly 160 may assume a first, deflated position in which the peripheral inflatable portion 166 assumes a diameter D1 smaller than the inner diameter of the main conduit 42, thus allowing the anchoring assembly 160 to freely displace within and along the main conduit 42, and a second, inflated position in which the peripheral inflatable portion 166 assumes a diameter D2 greater than the inner diameter of the main conduit 42, thereby applying pressure thereto and allowing, due to forces of friction, to suspend the membrane 40. In the inflated position, a gap 168 extends between the peripheral inflatable portion 166 and the wall of the main chamber 164.

In operation, the anchoring assembly 160 is displaced, in it deflated position, within the main conduit 42 until a desired location is reached. Thereafter, air (or any other gas for that matter) is provided through the air inlet 163 to the main chamber 164 and from there to the peripheral inflatable portion 166 via apertures 165. The introduction of air into the peripheral inflatable portion 166 causes it to inflate such that it increases its diameter from D1 to D2, thereby engaging the inner surface of the main conduit 42 of the membrane.

Figure 8D:
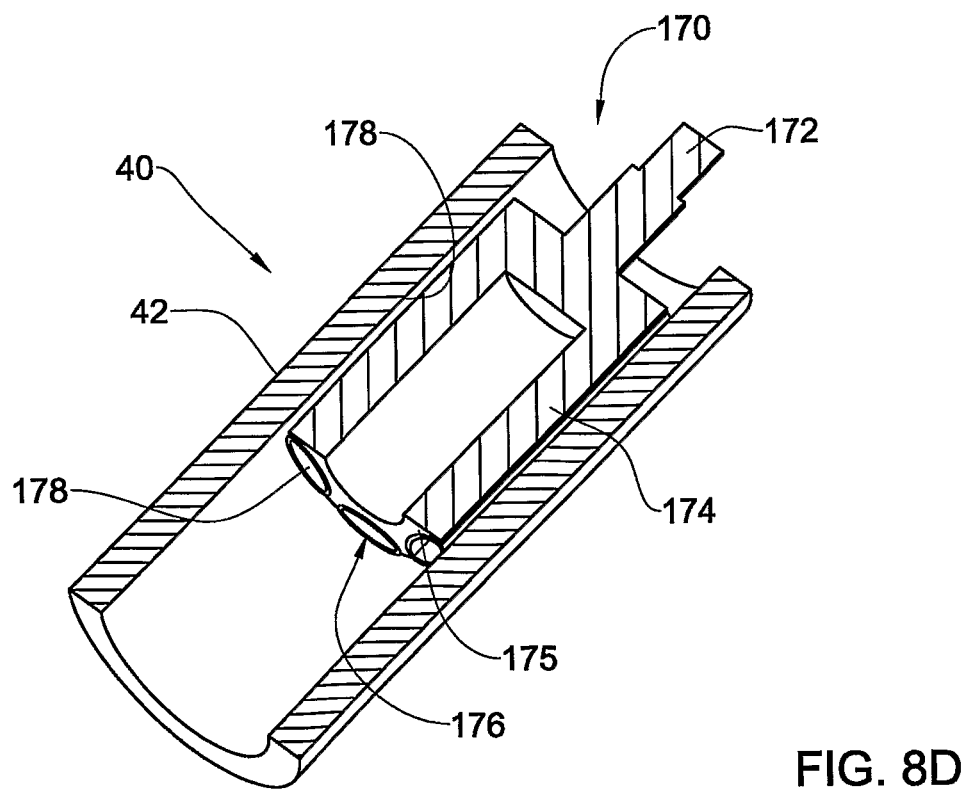
FIG. 8D is a schematic isometric cross-section view of a third embodiment of an anchoring assembly used in the anchoring arrangement shown in FIGS. 7A to 7C, when inserted into a conduit of a membrane to be anchored thereby.
Figure 8E:
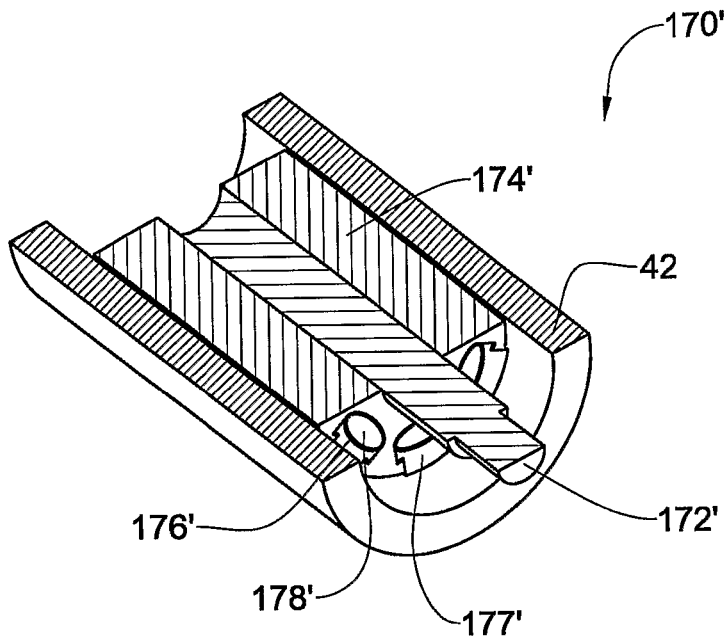
FIG. 8E is a schematic isometric cross-section view of a fourth embodiment of an anchoring assembly used in the anchoring arrangement shown in FIGS. 7A to 7C, when inserted into a conduit of a membrane to be anchored thereby.
Figure 8F:
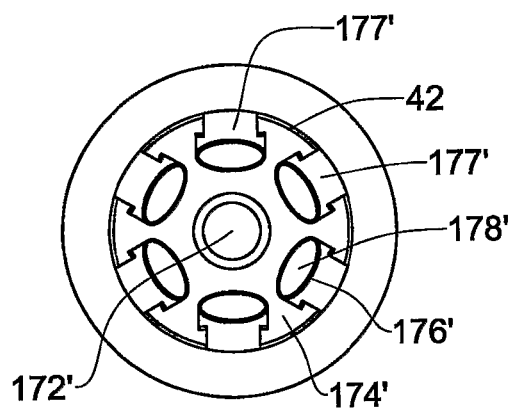
FIG. 8F is a schematic top view of the anchoring arrangement shown in FIG. 8E, when positioned within the conduit of a membrane.
Figure 8G:
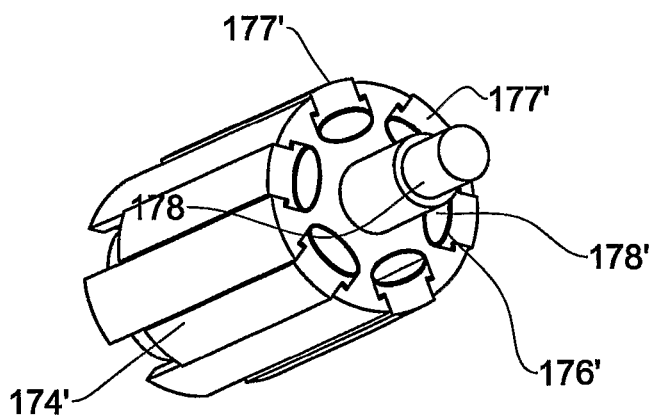
FIG. 8G is a schematic isometric view of the anchoring arrangement shown in FIG. 8E, when removed from the conduit of a membrane.

Turning now to FIG. 8D, a still further design of the second-stage anchoring assembly is shown generally designated as 170 and having a similar construction to the anchoring assembly 160 previously disclosed. However, in the present design the anchoring assembly comprises a main body 174 and a plurality of individually inflatable portions 176, adapted to receive air (or any other gas) not via the central line 172 and main body 174 but rather directly therein from an air source (not shown).

The main chamber 172 is formed, on the outer side thereof with a plurality of grooves 175 adapted to accommodate the inflatable portions 176. The inflatable portions 176 may be retained within the grooves 175 by any known method maintaining the impermeability of the inflatable portions 176. Alternatively, the inflatable portions may not be secured to the groves 175, but rather be suspended along with the main body 174 and anchored to it at a top end thereof.

Much like the previously disclosed anchoring assembly 170, the anchoring assembly 170 is adapted to assume a first, deflated position in which the peripheral inflatable portions 176 are deflated such that the diameter D1 of the anchoring assembly 170 is smaller than the inner diameter of the main conduit 42, thus allowing the anchoring assembly 170 to freely displace within and along the main conduit 42, and a second, inflated position in which the inflatable portions 176 assume a diameter D2 greater than the inner diameter of the main conduit 42, thereby applying pressure thereto and allowing, due to forces of friction, to suspend the membrane 40.

Figure 8H:
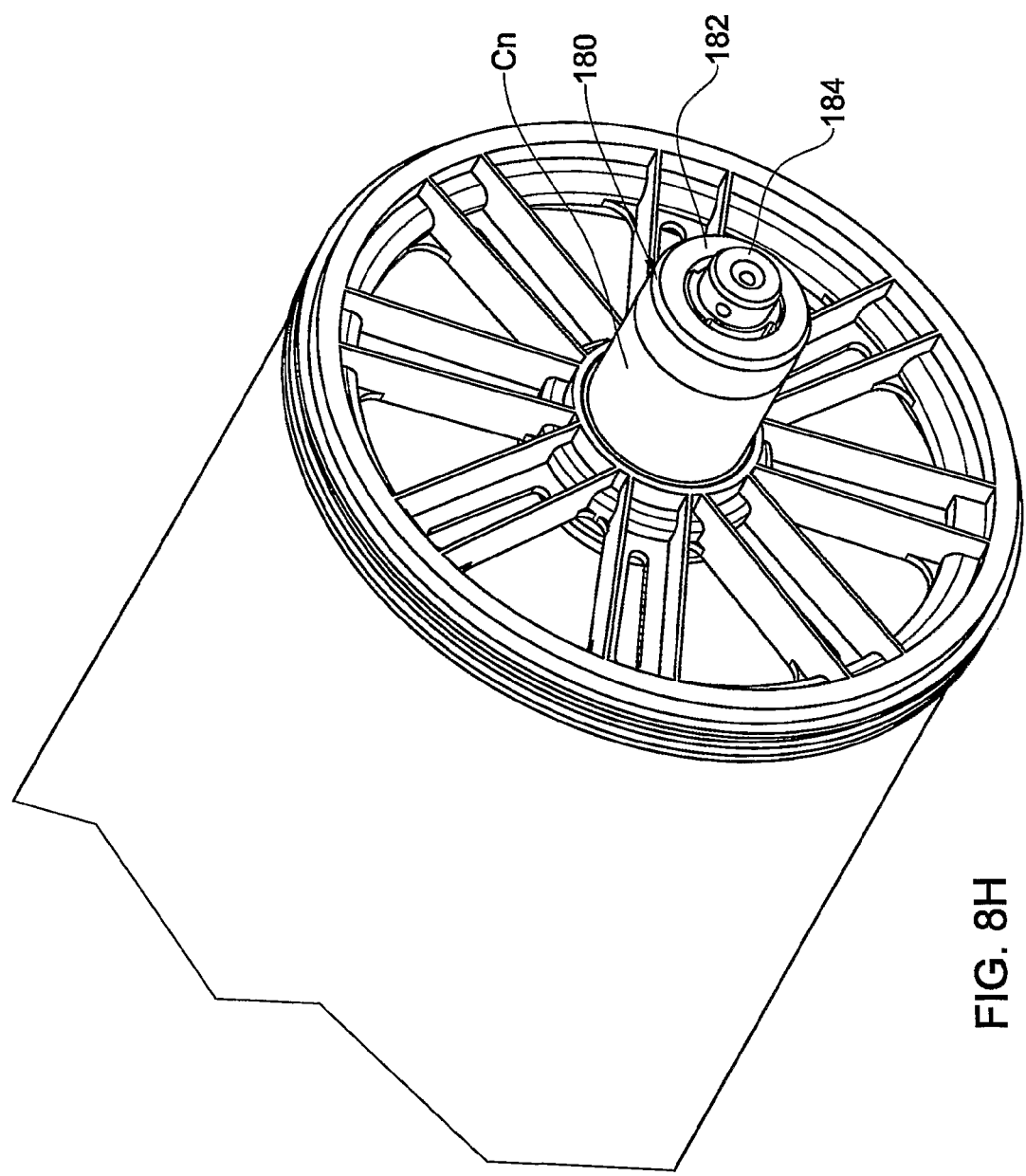
FIG. 8H is a schematic isometric view of a fifth embodiment of an anchoring assembly used in the anchoring arrangement shown in FIGS. 7A to 7C, shown in conjunction with a membrane to be anchored thereby.
Figure 8I:
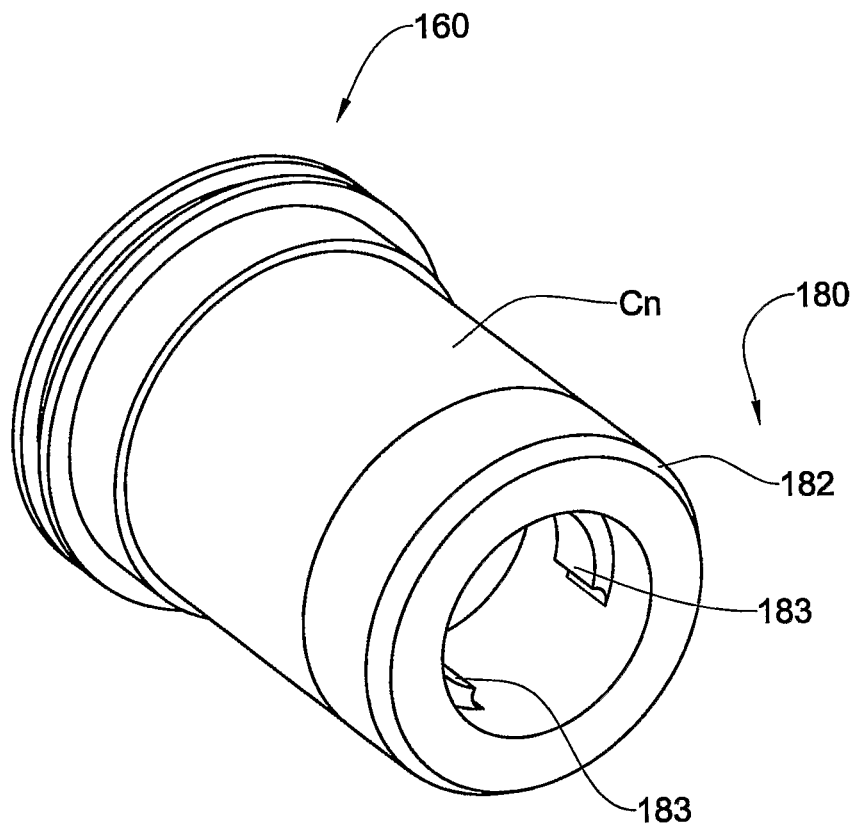
FIG. 8I is a schematic isometric view of the anchoring assembly shown in FIG. 8E, with the bayonet stub of the anchoring assembly being removed.
Figure 8J:
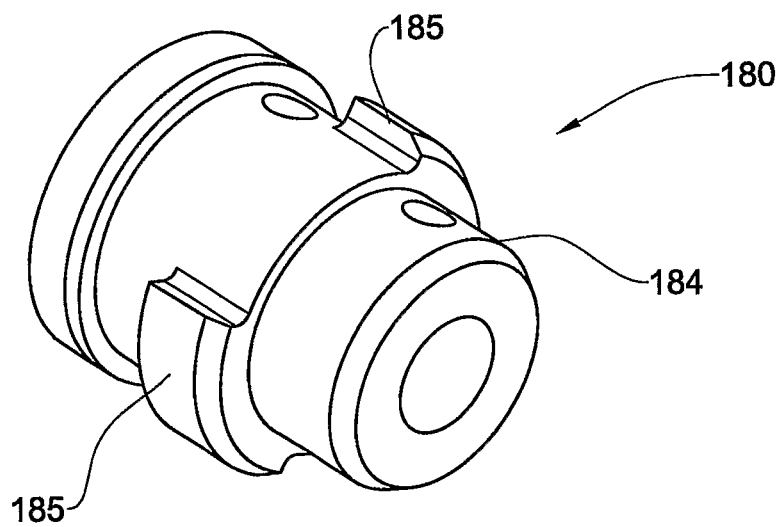
FIG. 8J is a schematic isometric view of the bayonet stub shown in FIG. 8E.

Turning now to FIGS. 8H to 8J, a still further design of the second-stage anchoring assembly is shown generally designated as 180 in the form of an anchoring adapter adapted for attachment to the proximal most membrane 40 positioned within the PV, i.e. the membrane the main conduit 42 of which is sealingly connected to the front permeate port 34F of the PV. More particularly, the proximal most membrane (lowermost) is formed with a fluid adaptor connecting the membrane to the front permeate line. This adapted is either replaced or modified so as to become attached to the anchoring adaptor 180.

The anchoring assembly 180 comprises a bayonet ring 182 adapted for fixed attachment to the end of the main conduit 42 such that it is positioned between this end and the front permeate port 34F, and a bayonet stub 184 adapted for fixed attachment to a central line (not shown), and bayonet engagement with the bayonet ring 184. The bayonet ring 182 and the bayonet stub 184 are formed with respective bayonet element 183 and 185.

Thus, when it is desired to remove one or more membranes 40 from the PV, the central line is lowered along with the bayonet stub 184 until the stub 184 reaches the bayonet ring 182. Thereafter, the bayonet stub 184 may engage the bayonet ring 182 whereby pulling the central line will entail displacement of the lower most membrane 40 along with any additional membranes located thereabove.

It should be pointed out that the anchoring assembly 180 as disclosed above is adapted for use in conjunction only with the lower most membrane. However, a similar anchoring assembly may be designed in which one or more bayonet rings are located between each two desalination membranes 40.

With respect to all previously disclosed second-stage anchoring assemblies 50, 150, 160, 170 and 180, it should be appreciated that the anchoring portion of the anchoring assembly may extend along the entire central line thereof, i.e. such that when inserted into the main conduit it extends the full length thereof. Alternatively, the anchoring assembly may be designed such that anchoring portion extends only a length equal to the length of a single membrane, or any multiple of that length.

In addition, with respect to the entire anchoring arrangement described above, it should be appreciated that the anchoring arrangement and the main crane may operate as separate elements. In other words, the anchoring arrangement may be used for displacing the membranes 40 from their position in the PV 30 to a predetermined amount so as to 'unjam' them, then returning the membranes to their original location within the PV and thereafter disengaging from the membranes 40. In this position, when the membranes are no longer 'lodged', the main crane may be used in conjunction with an anchoring assembly generally similar to the second-stage anchoring assembly previously disclosed in order to engage the membranes and removing them from the PV.

Figure 9A:
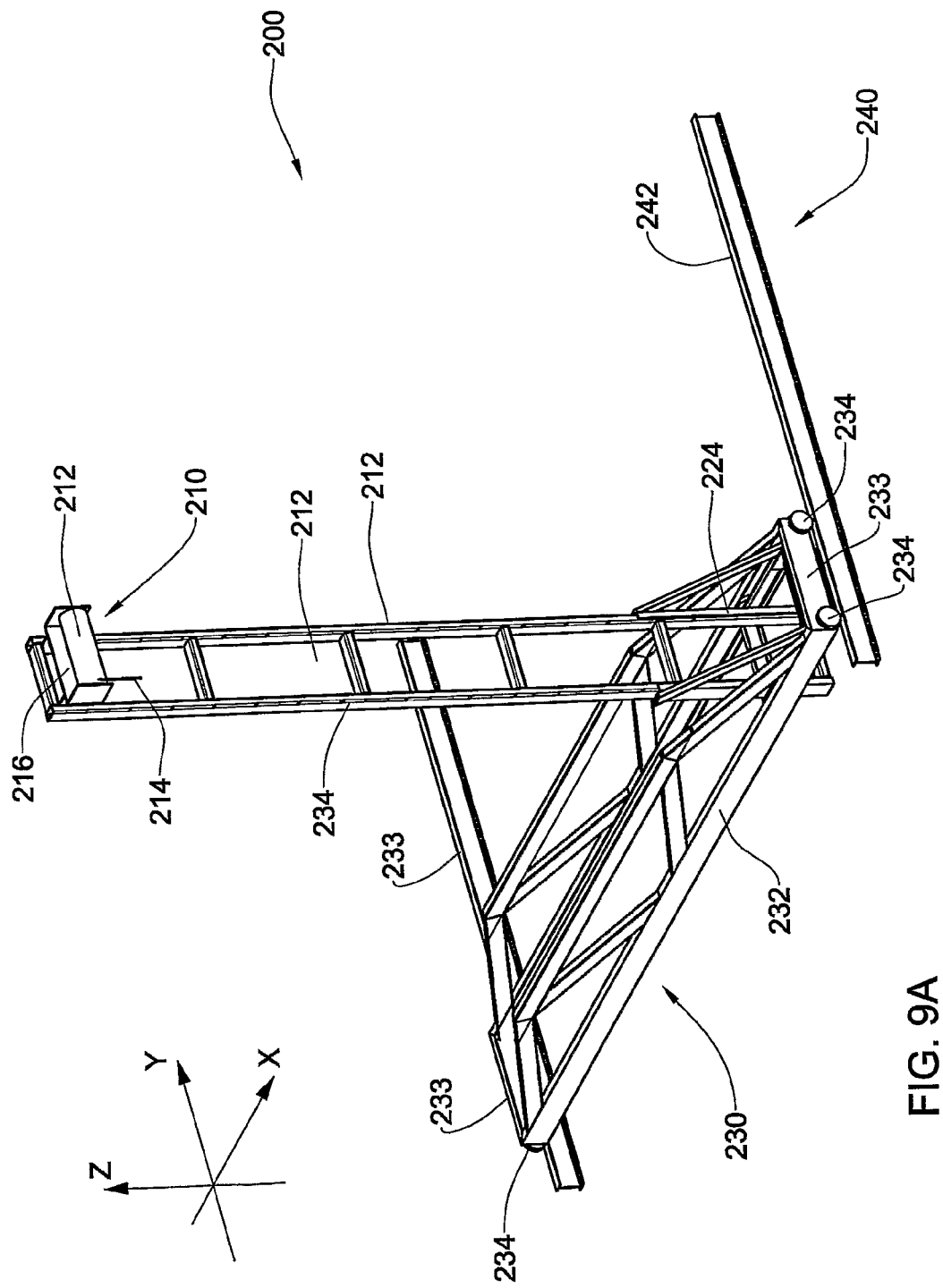
FIG. 9A is a schematic isometric view of a crane construction according to another aspect of the present invention.

Turning now to FIG. 9, a crane construction generally designated as 200 is shown comprising a wench mechanism 210, an up-down rail 220, a front-back rail 230 and a right-left rail 240.

The wench mechanism 210 comprises a wench 212 with a wench line 214 wrapped thereon, and a wench housing 216. The wench housing 216 is fixedly articulated to two rails 222 of the up-down rail 220.

The brackets 224 of the up-down rail 220 are slidingly received within parallel rails 232 of the front-back rail 230, allowing the entire up-down rail 220, along with the wench mechanism 210 to displace in the horizontal direction along the X axis. Extreme portions of the front-back rail 230 are fitted with wheels 234 adapted to roll along parallel rails 242 of the right-left rail 240, allowing the entire front back rail 230, along with the up-down rail 220 and the wench mechanism 210 to displace in the horizontal direction along the Y axis.

The entire crane construction is adapted to be positioned above the PV array of a desalination facility, such that above arrangement allows displacement of the wench mechanism 210 along the main X, Y and Z directions, so that the wench mechanism 210 may be brought to position above any one of the PVs and to a specific height thereabove.

An unloading operation using the wench mechanism and the two-stage anchoring arrangement will now be described. At the beginning of the unloading operation, the rails 222 along with the wench mechanism 210 are located in a downward position, i.e. the wench mechanism 210 is adjacent the brackets 224 and the rails 222 extend vertically below the rails 232 and 242. To the wench line 214 there is attached the two-stage anchoring arrangement (shown FIGS. 7A to 7C) including the first-stage anchoring assembly 110 and a second-stage anchoring assembly which may be any one of the anchoring assemblies 50, 150, 160, 170 or 180.

Thereafter, the entire up-down rail 220 is displaced along the rails 232 and 242 to bring it into position above the desired PV from which one or more membranes are to be removed. Once in position, the wench mechanism 210 is activated to lower the wench line 214 along with the two-stage anchoring arrangement towards the top end of the PV 30.

The two-stage anchoring arrangement is lowered until the first-stage anchoring assembly 110 may be fixed to the top end of the PV 30. Once fixed, the central line of the second-stage anchoring assembly is lowered until it engages the desired membrane as previously discussed with respect to FIGS. 8A to 8G. Once engaged, an released by the first-stage anchoring assembly 110, the wench line 214 is raised by the wench mechanism 210 to raise the two-stage anchoring arrangement along with suspended membrane/s to a desire amount.

Thereafter, the wench mechanism 210 along with the rails 222 are raised along the brackets 224, and the entire up-down rail 220 is brought to a new location by displacement along the rails 232 and 242.

It should also be appreciated that the up-down rail 220 along with the wench mechanism 210 may be an add-on arrangement mounted onto a conventional crane construction comprising the right-left rail 240 and the front-back rail 230, which is used for various tasks in the desalination facility other than loading/unloading of membranes.

Figure 9B:
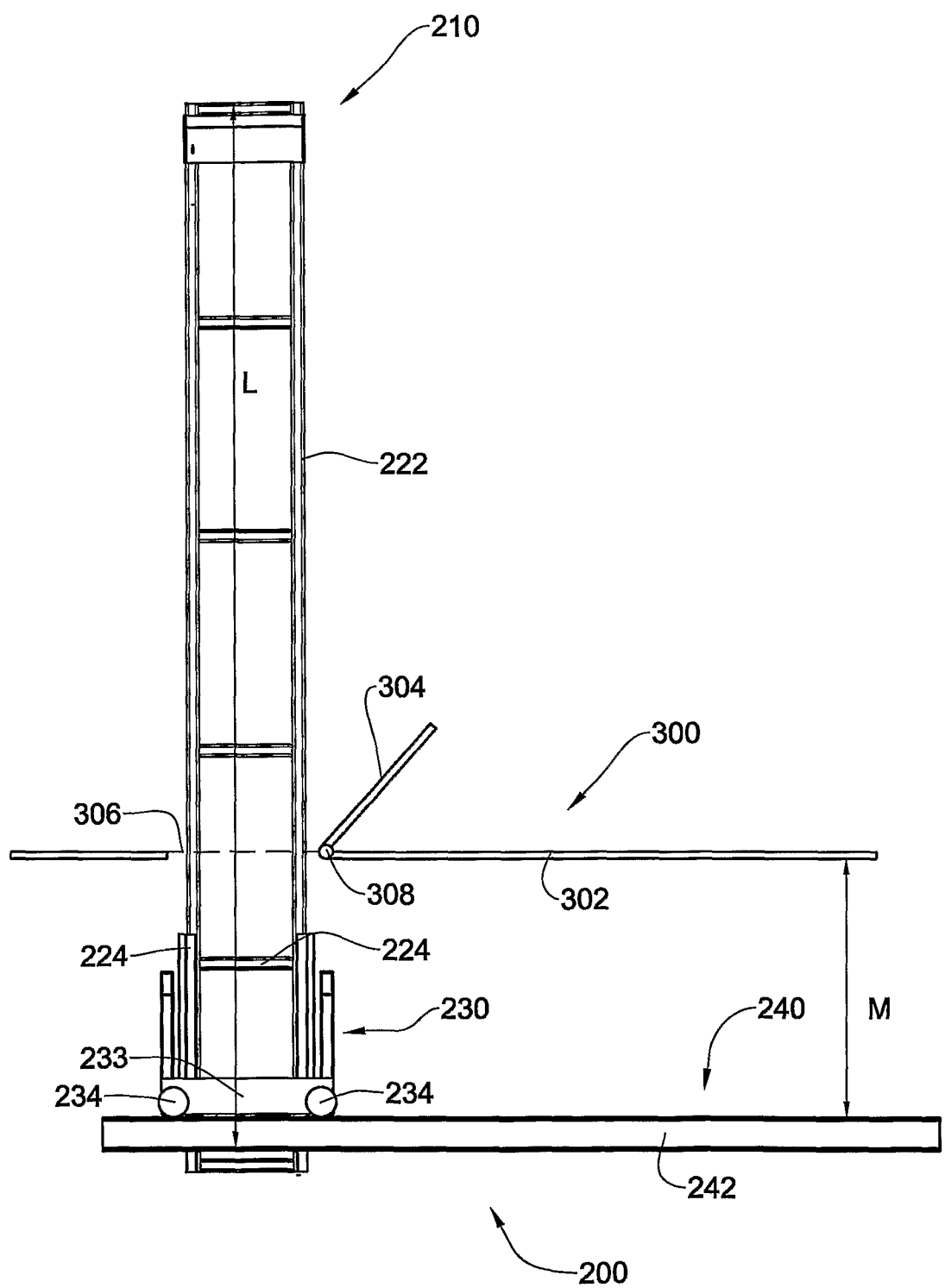
FIG. 9B is a schematic side view of the crane construction shown in FIG. 9A when positioned under a roof of a structure according to the present invention.

Turning now to FIG. 9B, the crane construction 200 is shown when located within a structure comprising a roof structure generally designated as 300, comprising a roof surface 302 and an adjustable portion 304. It is observed that the distance between the roof surface 302 and the rails 232 and 242 M is much smaller than the length L of the up-down rail 220. Thus, the adjustable portion 304 of the roof structure 300 is adapted to open up to the position shown in FIG. 9B, such that there is formed an opening 306 in the roof surface, allowing the rails 222 along with the wench mechanism 210 to displace upwards.

It is noted that although shown here to be opened via a hinge, the roof portion may be in the form of slidable slats, removable slats, a telescopic arrangement or the like.

It is also appreciated that the roof structure 300 may be formed with a plurality of adjustable roof portions 304 corresponding to the number of PVs 30 located within the structure, thereby allowing loading/unloading of membrane/s to/from any one of the PVs 30 located within the structure. In addition, the roof portions may be adapted to be opened above an entire row of PVs allowing the crane construction to displace freely along the row.

In addition, according to a particular design, the crane construction 200 may be positioned outside the structure, i.e. above the roof, and be lowered through the roof, e.g. through an open roof portion during loading/unloading of a membrane.

Furthermore, it is appreciated that such an arrangement provides for a considerably more compact design of the structure, and the roof thereof may be located in close proximity to the top ends of the PVs 30.

Figures 5A, 5B:
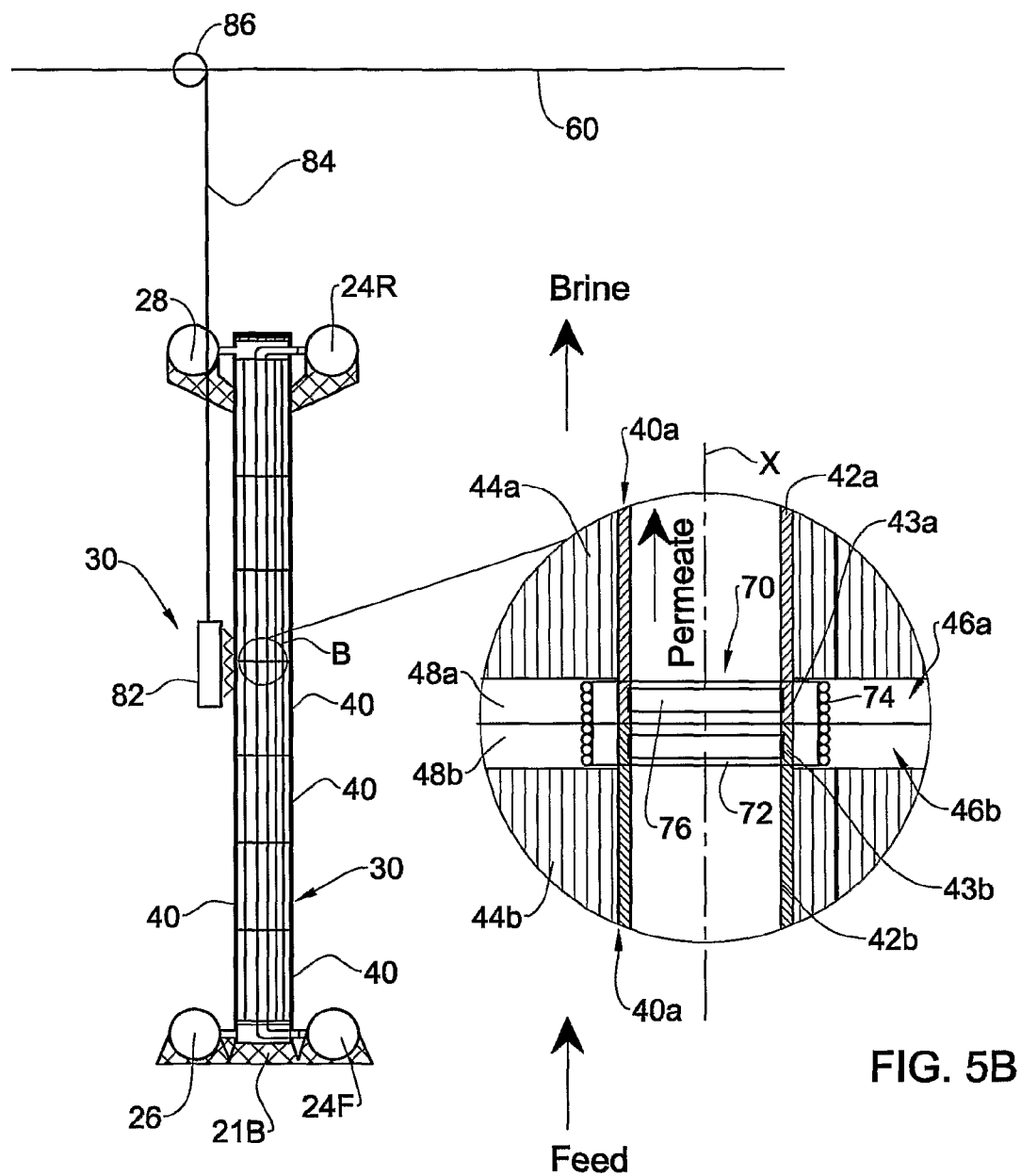
FIG. 5A is a schematic view of the PV shown in FIG. 4A, fitted with a reader according to an embodiment of the present invention.
FIG. 5B is an enlargement of detail B in FIG. 5A.

Turning now to FIGS. 5A and 5B, a plurality of membranes 40 are shown housed within the PV 30, being stacked one on top of another, with their permeate tubes 42 being in full alignment to form a common permeate tube of the PV 30. Each membrane 40, or at least the lowermost one, and the front permeate outlet port 34F, are designed so that upon the membrane's taking its position at the bottom end 32B of the PV 30, its permeate tube 42 is sealingly connected to the front permeate outlet port 34F. Similarly, each membrane 40, or at least the uppermost one, and the cover 31 are designed so that upon placing the cover 31 in its position at the top end 32T of the PV 30, the rear permeate outlet port 34R formed in the cover is sealingly connected to the permeate tube 42 of the uppermost membrane.

The membranes 40 are further adapted for connection to each other. For this purpose, the permeate tube 42, and the outer shell 46 of each membrane 40 extends axially more than the spiral wound elements 44, i.e. each permeate tube 42 and outer shell 46 have an extension portion 43 and 48 beyond the spiral wound element 44. Thus, when two membranes 40a, 40b are positioned as shown in FIG. 5B, the extension portions 43a, 43b of their permeate tubes 42a and 42b come in contact with one another, and so do the extension portions 48a, 48b of their outer shells 46a and 46b.

The weight of the upper membrane 40a is therefore supported mostly by the outer shell 46b of the lower membrane 40b. For this purpose, the outer shell 46 of each the membrane 40 is designed with a sufficient thickness, and of proper material to allow the outer shell 46 to support the weight of a desired number of membranes 40 stacked thereon. Such a material may be, for example, FRP fibers and/or epoxy.

FIG. 5B shows one possible manner of coupling the two membranes 40a, 40b to one another. This is achieved by using a coupling 70 in the form of a fastener 72 mounted on exterior of the extension portions 43a, 43b of the permeate tubes 42a, 42b for providing secure sealed engagement therebetween. The fastener 72 of the coupling 70 may alternatively be mounted on the interior of the extension portions 43a, 43b of the permeate tubes 42 (not shown).

The coupling may optionally comprise a sensing system for measuring operational parameters of the membranes 40 and/or fluid passing therethrough, for determining the functioning condition of the membranes.

FIG. 5B shows one such sensing system comprising two sensors 74 and 76, adapted to respectively measure the quality and flow rate of water passing through the coupling 70 in a manner known per se.

Each sensor 74, 76 may be operated continuously, measuring parameters throughout the operation of the desalination system 20. Alternatively, each sensor 74, 76 may be adapted to operate in bursts, sampling the above parameters along predetermined periods of time, or upon prompt from an external source.

Each sensor 74, 76 is also adapted to transmit data produced based on the measurement taken thereby, to an external source, for example a reader located outside said PV 30 as will be further explained with reference to FIG. 5A.

The sensors 74, 76 may be adapted to be operated using an internal power source such as, for example, a battery, or an external source e.g. by electrical induction therefrom.

It should be indicated that the location of the sensors 74, 76 is not restricted to the coupling 70 and they may be located within the permeate tube 42, within the spiral wound element 44 and even on the inner sidewall of the PV 30. In general, the sensors 74, 76, or any other devices for measuring operational parameters of the membranes 40 and/or fluid passing therethrough, may be located anywhere along the axial extension of the membranes 40. It should however, be appreciated that sensor 76 adapted to measure the quality of water passing through the PV 30 is required to come in direct contact with the fluid, e.g. feed, permeate, reject, passing through the membranes 40.

With reference to FIG. 5A, the system 20 may be further provided with a data reading arrangement 80 comprising a reader 82, a cable 84 and a displacement mechanism 86 adapted for connection to an anchoring line 60 and optionally to a mainframe computer (MFC). The data reading arrangement 80 is designed so as to be horizontally displaceable by the displacement mechanism 86, and the reader 82 is designed so as to be vertically displaceable by the cable 84.

The reader 82 is adapted to constitute a power source for the sensors 74, 76, whereby upon being positioned adjacent one of the sensors, electrical induction between the two articles activates the sensor 74, 76 to take a measurement and provide the measured data back to the reader 82. Transfer of the data from the sensor to the reader is performed in a wireless manner.

In assembly, the displacement mechanism 86 is positioned above an array of vertically oriented PVs 30 of the system 20 all of which may have sensors as described above. In order to collect a measurement from one of the sensors 74, 76 accommodated within one of the vertically disposed PVs 30, the following steps are performed:
 a) horizontally displacing the displacement mechanism 86 for its location above a desired PV 30;
 b) displacing the reader 82 downwards along the PV 30 to be aligned with the sensor 74, 76;
 c) operating the sensor 74, 76 by the reader 82, to take the required measurement;
 d) collecting data from the sensor 74, 76 by the reader 82; and
 e) transferring the data to the MFC.

In practice, the above steps may be performed for every one of the membranes 40 of each PV 30 in order to receive as much data as possible.

In general, the vertical orientation of the PVs 30 facilitates the manipulation of accessories such as the reader 82 and anchoring arrangement 50, and of the membranes 40. This in turn eliminates the need for intricate transport construction for horizontal displacement of these elements, used in known desalination systems with horizontally oriented PVs.

Figure 6A:
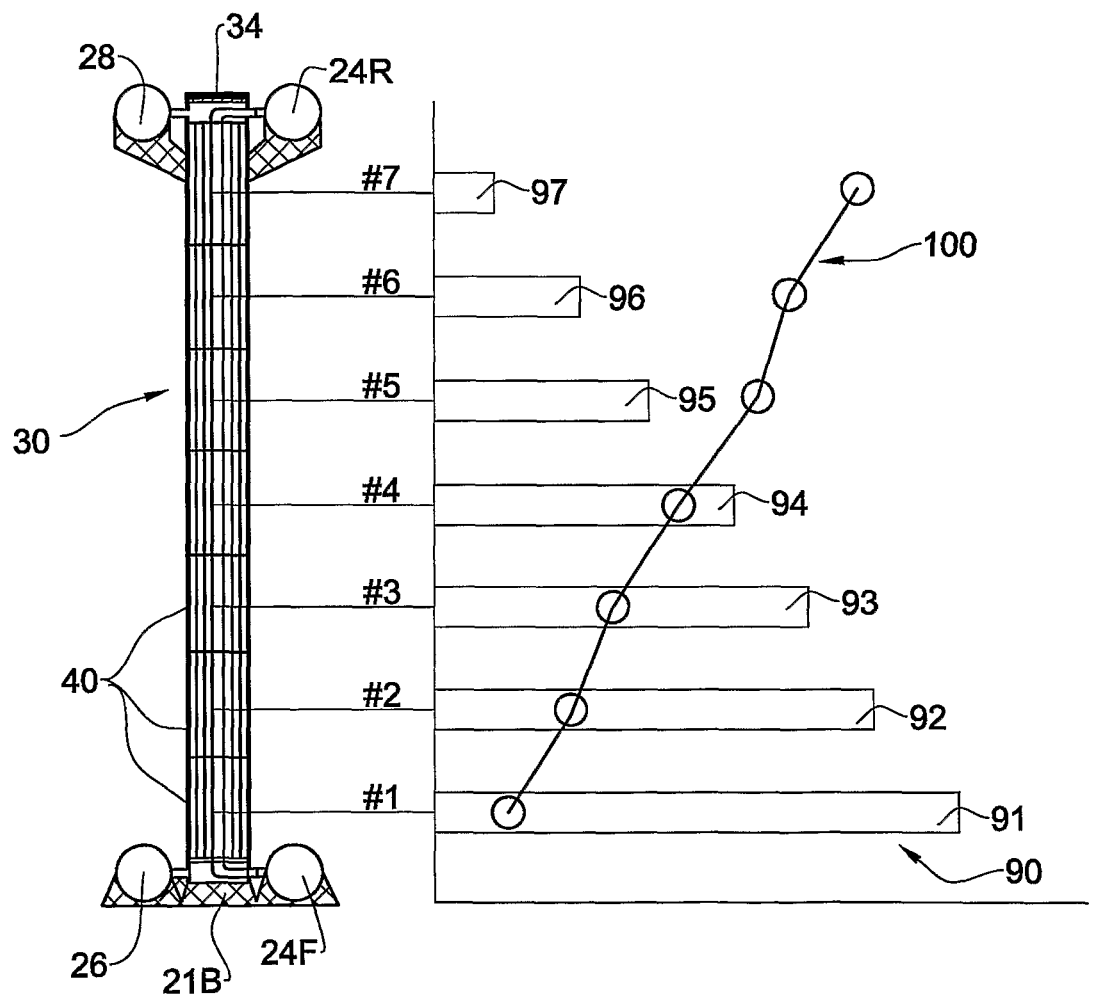
FIG. 6A is a schematic view of the PV shown in FIG. 4 with an example of graphical representation of measurements collected by the reader shown in FIG. 5A.

FIG. 6A shows measurements which may be taken from membranes #1 to #7 of a single PV 30 by the reader 82. The set of measurements 90 includes measurements 91 to 97 denoting the flow rate through the spiral wound element 44, i.e. osmosis rate, and the set of measurements 100 includes measurements 101 to 107 denoting salinity on either the reject or the permeate sides of the spiral wound element 44, each measurement corresponding to one of the membranes #1 to #7.

As may be observed from the above taken measurements, as water progresses through the PV 30 the salinity of the reject increases while the osmosis rate through the spiral wound element 44 decreases. This, however, does not indicate to an operator of the system 20 of any malfunction or damage in any one of the membranes #1 to #7.

Figure 6B:
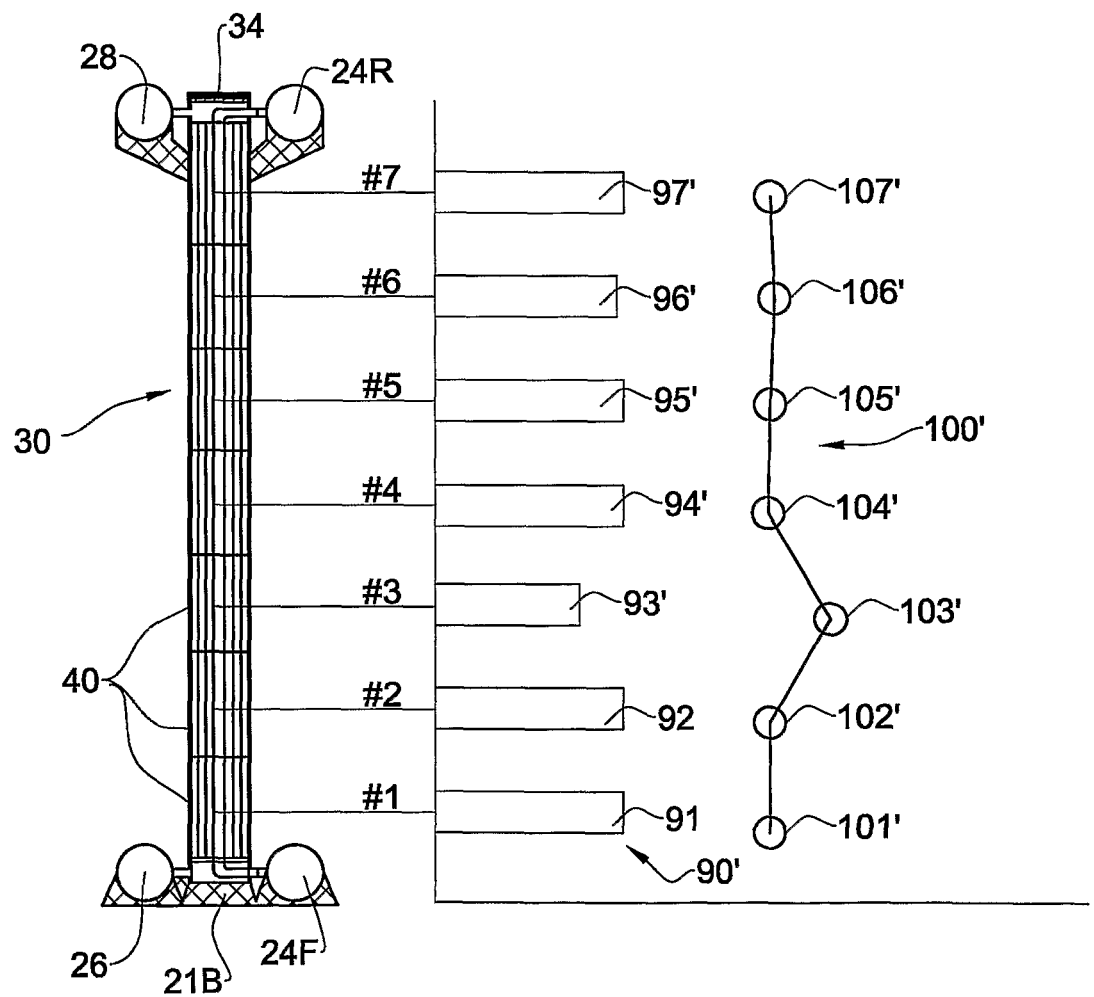
FIG. 6B is a schematic view of the PV of FIG. 6A with the measurements shown after analysis thereof using an appropriate algorithm.

Turning to FIG. 6B, the measurements are shown again after performing an analysis of the data including normalization of the values thereof. It may now be observed that membrane #3 demonstrates a lower osmosis rate and higher salinity on the reject side than all the other membranes #1 to #2 and #4 to #7. This might indicate to operator that membrane #3 is damaged and needs to be replaced. It would be noted here that the analysis of the data allows providing a graphic display of the functionality of the PV's membranes, without the operator being required to understand the true meaning of the displayed measurements. In other words, the operator is simply required to identify a membrane which demonstrated a functionality which is exceptional to the other membranes.

It would be appreciated that all operations described hereinbefore, including loading of a PV 30, collecting measurements, detecting a faulty membrane, and replacing a faulty membrane may be accomplished by a completely automated process controlled by the MFC, without requiring an operator to be present. For example, the MFC may be programmed such that the data reading arrangement 80 systematically collects measurements from all membranes 40 of the system 20, the MFC analyzes the collected data, and upon detection of a faulty membrane, automatic replacement of the membrane is performed as described above.

For this purpose, each of the PVs 30, and each of the membranes 40 may be equipped with an indexing module, denoting the exact location of the PV 30 and membrane 40 within a specific PV 30. The indexing allows the MFC to pin-point the exact location of a membrane 40, indicating to the anchoring module 56 and displacement mechanism 86 exactly where to be displaced.

Figure 10A:
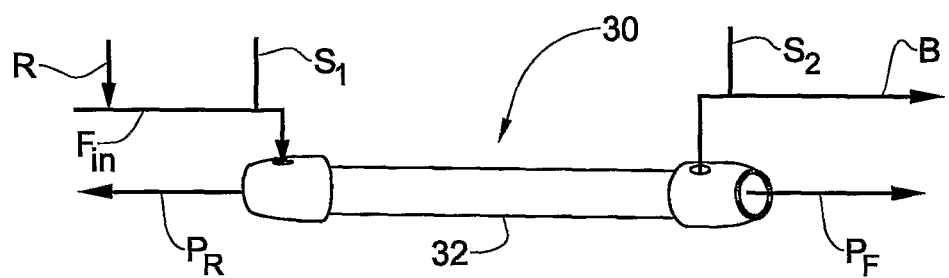
FIG. 10A is a schematic isometric view of a PV comprising a sensing arrangement according to still a further embodiment of the present invention.
Figure 10C:
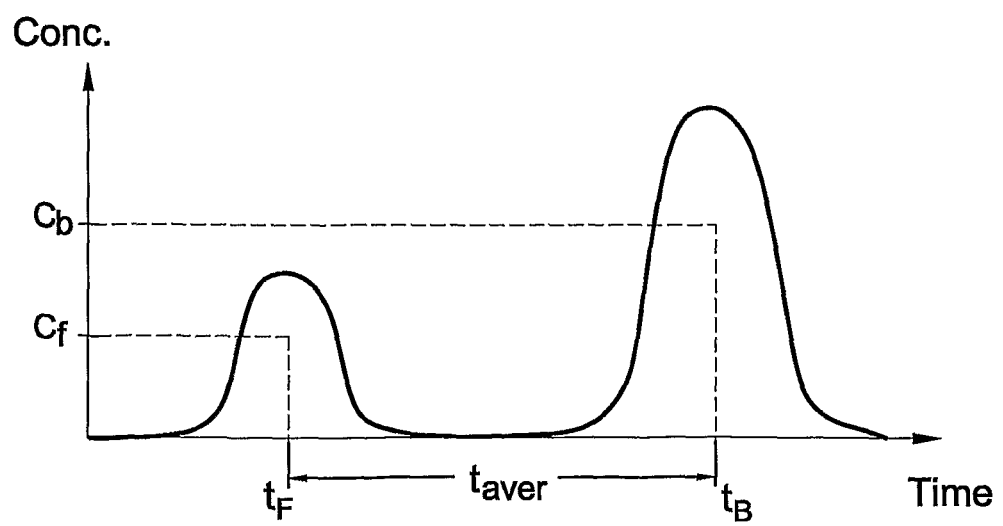
FIG. 10C is a schematic representation of data gathered by the sensing arrangement shown in FIG. 10A.
Figure 10B:
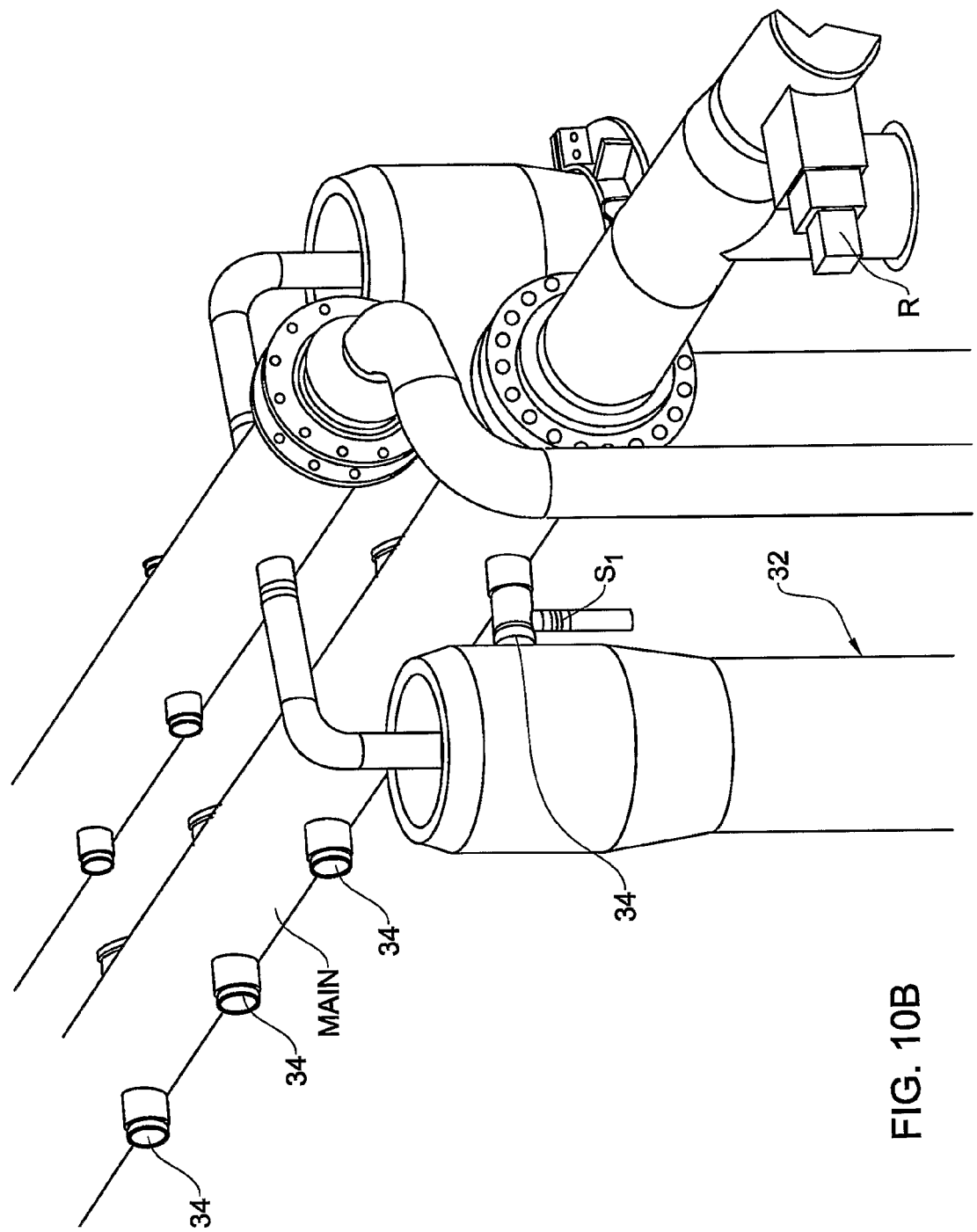
FIG. 10B is a schematic isometric view of the PV shown in FIG. 10A when attached to a common feed line.

Turning now to FIGS. 10A to 10C, there are demonstrated a structure and method for measuring flow rate of fluid within the PV 30. The PV is shown comprising a feed inlet $F_{in}$ attached to a feed line, a brine outlet B attached to a brine line, a front products $P_F$ outlet and a rear product outlet $P_R$. The feed line is provided with a test substance inlet R and a first test sensor $S_1$, and the brine line is provided with a second test sensor $S_2$.

In operation, in order to measure flow rate, a test substance, e.g. Rhodamine, is introduced into the test substance inlet R, wherein it is first detected by the first test sensor $S_1$ and thereafter passed along with the fluid to be desalinated towards the brine outlet B of the PV, where it is detected by the second test sensor $S_2$.

Each of the sensors $S_1$, $S_2$ provides two measured parameters of the test substance—its concentration C, and the time of measurement t. Thus, the chart shown in FIG. 10C may be produced denoting the average time $t_F$ in which the Rhodamine was introduced into the PV and its concentration $C_F$ at that time, and the average time $t_B$ the Rhodamine has exited the PV and its concentration $C_B$ at that time.

From the above data, obtained for each of the PVs, the flow rate Q for each PV may be calculated by the following set of equations:

Membrane mass balance equation:

$$Q_{Feed} = Q_{Product} + Q_{Brine};$$

Rhodamine mass balance equation:

$$Q_{Feed} \cdot C_{Feed} = Q_{product} \cdot C_{Product} + Q_{Brine} \cdot C_{Brine};$$

It is noted that the Rhodamine molecules are too big in order to penetrate through the wall of the membrane, and therefore all Rhodamine entering the PV remains on the brine side of the membrane, and hence, the concentration $C_{product} = 0$.

Thus, the following equations are yielded:

$$Q_{Feed} \cdot C_{Feed} = Q_{Brine} \cdot C_{Brine} \Rightarrow Q_B = Q_F \cdot \frac{C_F}{C_B};$$

The recovery rate is given by the formula $$R = \frac{Q_P}{Q_F}$$

The above yields the following equations:

$$Q_F = Q_F \cdot \frac{C_F}{C_B} + Q_P \text{ and } R = 1 - \frac{C_F}{C_B} = \frac{Q_P}{Q_F}.$$

Using the equations denoting the flow rate through the PV it may be stated that:

$$Q_{Ave.} = \frac{Q_F + Q_B}{2} = A \cdot \frac{L}{\Delta t},$$

where A is the area of the cross section for fluid flow, L is the length of the PV and $\Delta t$ is denoted by $t_F$-$t_B$.

Thus, the following equation is yielded:

$$Q_F = \frac{2A \cdot \frac{L}{\Delta t}}{1 + \frac{C_F}{C_B}},$$

and equation in which all parameter are either known from the design of the PV or obtained by the sensors $S_1$, $S_2$.

The above arrangement of sensors and calculation provides the flow rate for each of the PVs.

In addition, it should be appreciated that using such a method for measuring the flow rate eliminates the need for costly flow meters and additional pipe design required for use thereof (generally, in order to measure flow rate properly, a flow meter is required to be positioned within a pipe segment in which non-turbulent flow takes place, requiring in turn a pipe segment of 2D before the flow meter and 5D after the flow meter, D being the diameter of the pipe). This contributes considerably to a more compact and space-efficient design of the entire desalination system.

In addition, with reference to FIG. 10B, it is observed that the PV receives the feed inlet from a common feed line, associated with each and every PV in the same row (other PVs not shown). Thus, the common feed line has a first end associated with the first end of the PV row, and a second end associated with the second end of the PV row. In the present example, the common feed line is adapted to receive the feed fluid from both the first end and the second end (double-sided feed), thus allowing reduction of the diameter D of the pipe.

Reducing the diameter of the pipe allows a more dense spacing between corresponding rows of PVs.

Figure 11A:
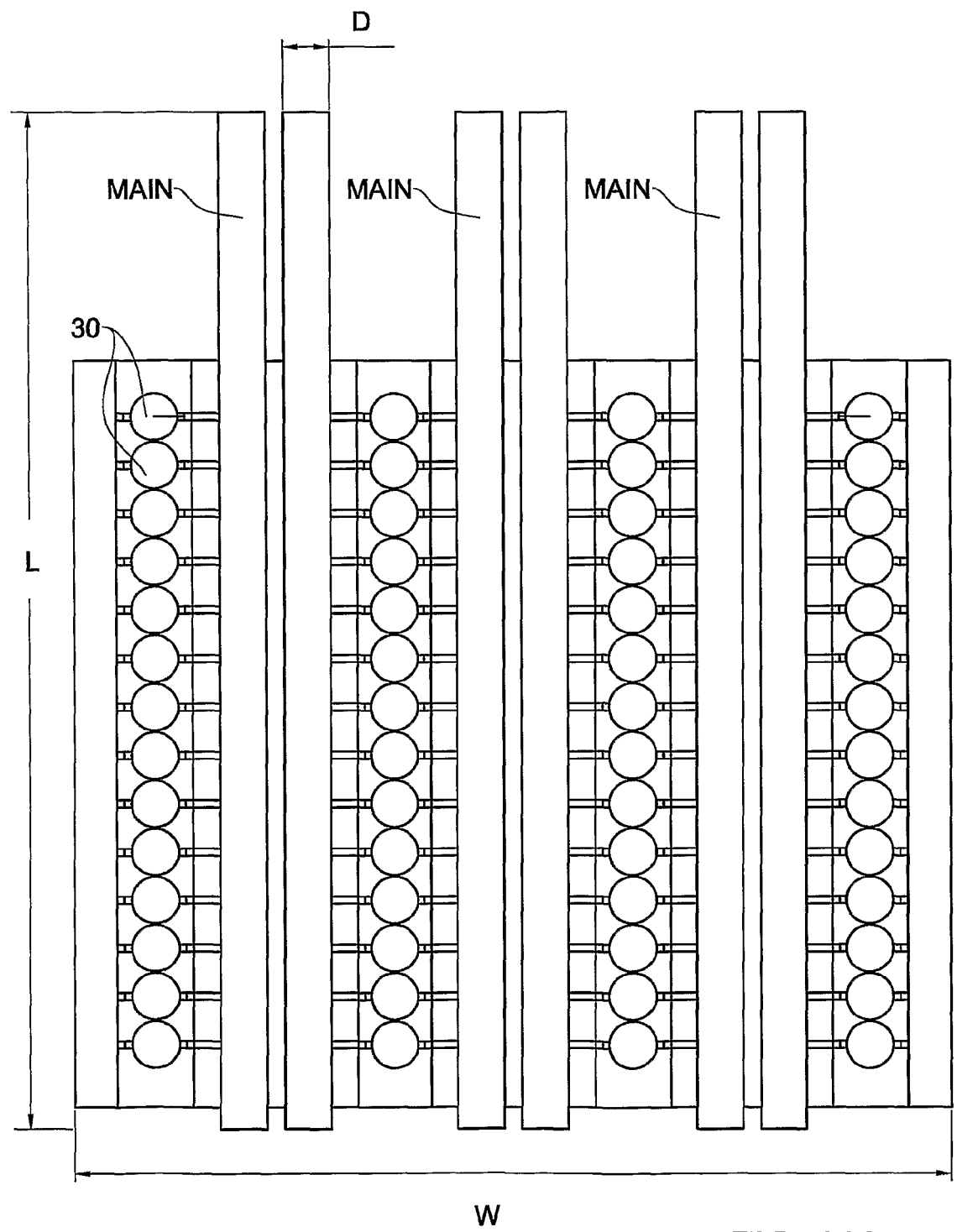
FIG. 11A is a schematic top view of a desalination system comprising a plurality of PVs according to one arrangement.
Figure 11B:
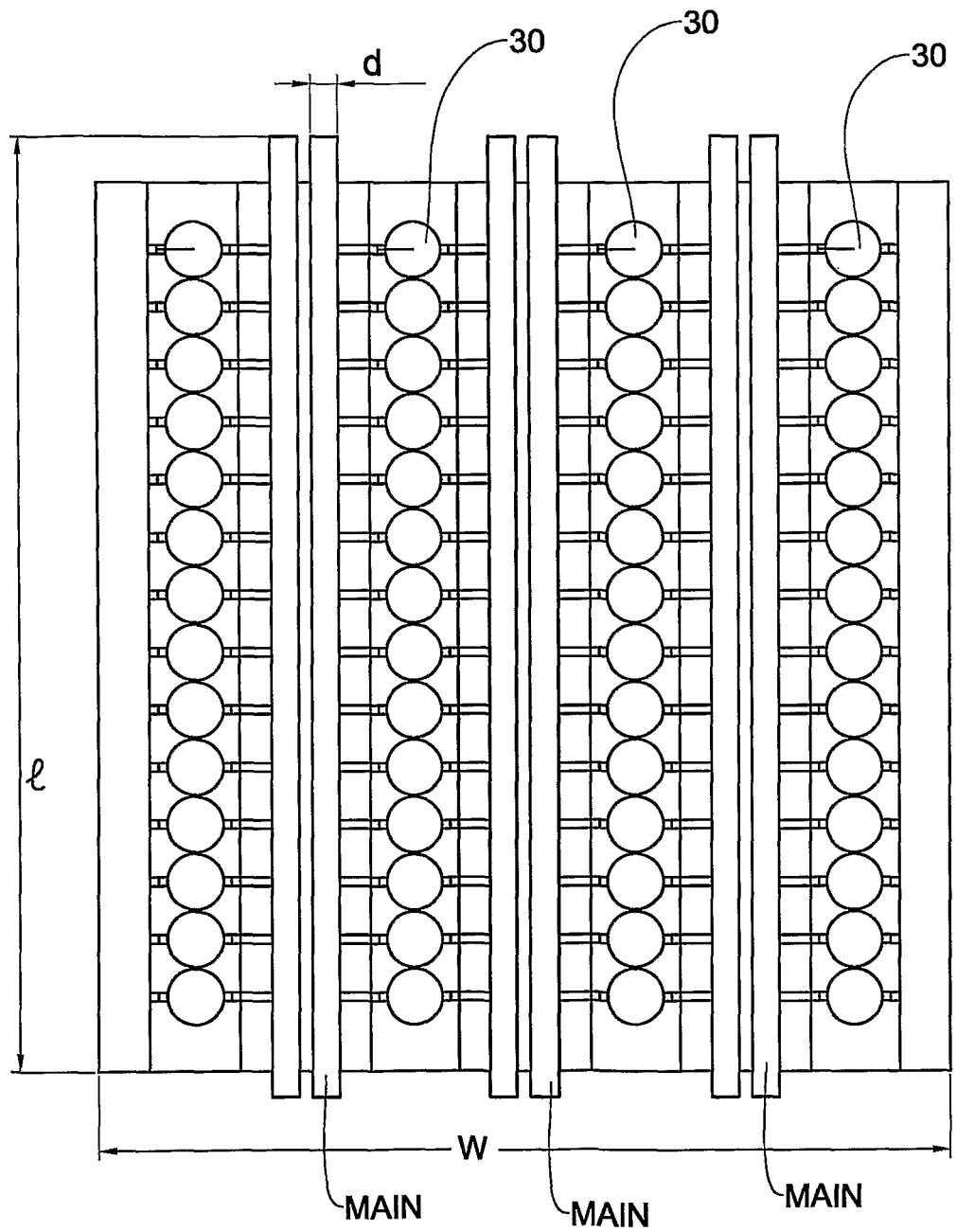
FIG. 11B is a schematic top view of a desalination system comprising a plurality of PVs according to another arrangement of the invention.

With particular reference to FIGS. 11A and 11B, FIG. 11A demonstrates a desalination system comprising a plurality of rows of PVs in which flow meters are used along with one-sided feed, and FIG. 11B demonstrates another desalination system comprising the same number of PVs, in which a test substance is used along with a double-side feed.

In FIG. 11B, the length of the entire system is L, and the width is W, this for a common feed line of diameter D. It is also observed that the common feed line CFL has a diameter D. To the contrary, in FIG. 11B, the CFL has a diameter d=D/2, thus allowing for a more dense and space-efficient arrangement. Furthermore, the use of Rhodamine instead of a flow meter allows eliminating the additional segment AS of the CFL, yielding a desalination system of dimensions l<L, and w<W.

Those skilled in the art to which this invention pertains will readily appreciate that numerous changes, variations, and modification can be made without departing from the scope of the invention, mutatis mutandis.

The invention claimed is:

1. A desalination system comprising:
a plurality of vertical pressure vessels (PVs), each in fluid communication with a feed pipe, a brine pipe and at least one permeate pipe, and each comprising at least five membrane elements having a diameter of at least 16 inches set one upon the other in a column, wherein each membrane element is secured with an o-ring, such that each membrane element supports the membrane elements positioned above it, to yield a load upon each but a top membrane element, wherein each PV holds one column of membrane elements, wherein each membrane element is arranged to produce permeate from feed water and to convey the permeate through a central vertical conduit in the membrane element, and wherein the central vertical conduits of all membrane elements per PV are in fluid communication with each other and with the at least one permeate pipe;
a feeding module arranged to deliver feed water via the feed pipe to the PVs;
a brine collecting module arranged to receive brine via the brine pipe from the PVs; and
a permeate module arranged to receive permeate via the at least one permeate pipe from the membrane elements in the PVs,
wherein the membrane elements are configured to support the load of the membrane elements positioned thereupon, and
wherein the columnar arrangement of the membrane elements in the vertical PVs is configured to allow for thermal expansion of the membrane elements while limiting, by generating the loads upon the membrane elements and without any additional limiting mechanism, a movement of the membrane elements upon abrupt feed water flow changes, and further to yield a full evacuation of foam produced during cleaning of the membrane elements
wherein at least some of the PV's include a plurality of sensors, each sensor associated with one of the membrane elements in the PV and arranged to measure a flow and a salinity of feed water in the PV at the sensor's position upon external power induction, the sensors further arranged to communicate the measurements;
at least one measurement device arranged to inductively provide power to sensors in a specified range therefrom and receive measurements therefrom; and
a data processor arranged to receive the measurements from the at least one measurement device and calculate therefrom vertical flow and salinity profiles in the PV, to yield an indication of a faulty membrane element.

2. The desalination system of claim 1, wherein all PVs are parallel and in a same height, such as to allow their maintenance to be carried out at two levels—an upper level comprising a connection to the feed pipe and a connection to one permeate pipe, and a lower level comprising a connection to the brine pipe and a connection to a second permeate pipe.

3. The desalination system of claim 1, wherein the feed pipe has two ends, and wherein the feeding module is arranged to deliver feed water to the PVs through the feed pipe from both ends of the feed pipe, to enhance a throughput cross-section to feed pipe cross-section ratio in the desalination system.

4. The desalination system of claim 1, further comprising:
a test unit comprising:
 a release unit configured to release a test substance at a specified concentration and during a specified period into feed water delivered to a specified group of PVs; and
 per each PV in the specified group, a first sensor at an entrance to the PV and a second sensor at the exit from the PV, both sensors arranged to measure over time a concentration of the test substance, and
a data processor connected to the sensors, arranged to calculate from the measurements an entering signal and an exiting signal, each characterized by a weighted concentration and a peak time, and to calculate a throughput of the PV therefrom, and further arranged to derive from the throughput an indication of a PV having a faulty membrane element.

5. The desalination system of claim 1, further comprising a loading mechanism arranged to load the membrane elements into the vertical PV.

6. The system of claim 1, wherein said feed pipe delivers seawater to said membranes for desalination.

7. A method of using large membrane elements for desalination, comprising:
providing the desalination system of claim 1;
loading a vertical pressure vessel (PV) with at least five membrane elements having a diameter of at least 16 inches set one upon the other in a column, such that each PV holds one column of membrane elements and such that each membrane element supports the membrane elements positioned above it, to yield a load upon each membrane element, wherein the membrane elements are configured to support the load of the membrane elements positioned thereupon; and
delivering feed water through the column of membrane elements to yield brine and permeate,
wherein the columnar arrangement of the membrane elements in the vertical PVs is configured to allow for thermal expansion of the membrane elements while limiting, by generating the loads upon the membrane elements and without any additional limiting mechanism, a movement of the membrane elements upon abrupt feed water flow changes, and further to yield a full evacuation of foam produced during cleaning of the membrane elements.

8. The method of claim 7, further comprising maintaining the PVs at two levels only.

9. The method of claim 7, further comprising delivering the feed water to the PVs from two directions to enhance a throughput to feed pipe cross-section ratio of the feed water delivery.

10. The method of claim 7, further comprising:
releasing a test substance at a specified concentration and during a specified period into feed water delivered to a specified group of PVs;
measuring over time a concentration of the test substance at the entrance and at the exit of each PV;
calculating, from the measurements, an entering signal and an exiting signal, each characterized by a weighted concentration and a peak time;
calculating a throughput of the PV from the calculated signals; and
deriving, from the calculated throughput, an indication of a PV having a faulty membrane element.

11. The method of claim 7, further comprising:
measuring a flow and a salinity of feed water at a plurality of positions in the PV;
calculating, from the measurements, vertical flow and salinity profiles in the PV, to yield an indication of a faulty membrane element.

12. The method of claim 11, wherein the measurement is carried out by external power induction.

13. The method of claim 7, wherein the membrane elements are loaded either singly or groupwise into the vertical PV.

* * * * *